(12) United States Patent
Kaethner et al.

(10) Patent No.: US 11,508,100 B2
(45) Date of Patent: Nov. 22, 2022

(54) PROVIDING A DIFFERENCE IMAGE DATA RECORD AND PROVIDING A TRAINED FUNCTION

(71) Applicant: Siemens Healthcare GmbH, Erlangen (DE)

(72) Inventors: Christian Kaethner, Forchheim (DE); Markus Kowarschik, Nuremberg (DE); Michael Manhart, Fuerth (DE)

(73) Assignee: SIEMENS HEALTHCARE GMBH, Erlangen (DE)

( * ) Notice: Subject to any disclaimer, the term of this patent is extended or adjusted under 35 U.S.C. 154(b) by 389 days.

(21) Appl. No.: 16/736,058

(22) Filed: Jan. 7, 2020

(65) Prior Publication Data

US 2020/0226801 A1 Jul. 16, 2020

(30) Foreign Application Priority Data

Jan. 11, 2019 (DE) .......................... 102019200270.6

(51) Int. Cl.
*G06T 11/00* (2006.01)
*A61B 6/00* (2006.01)

(52) U.S. Cl.
CPC .......... *G06T 11/003* (2013.01); *A61B 6/4014* (2013.01); *A61B 6/481* (2013.01);
(Continued)

(58) Field of Classification Search
None
See application file for complete search history.

(56) References Cited

U.S. PATENT DOCUMENTS 7,330,532 B2 2/2008 Winsor
2006/0198491 A1* 9/2006 Taguchi ................ A61B 6/027
378/15

(Continued)

FOREIGN PATENT DOCUMENTS

| CN | 107847209 A | 3/2018 |
|----|----|----|
| CN | 108022272 A | 5/2018 |
| DE | 102019200270 A1 | 7/2020 |
| EP | 3591617 A1 | 1/2020 |
| WO | WO 2019149711 A1 | 8/2019 |

OTHER PUBLICATIONS

J.C. Montoya et al.: "3D Deep Learning Angiography (3D-DLA) from C-arm Conebeam CT", Original Research Interventional, AJNR, 2018.
(Continued)

*Primary Examiner* — Hoon K Song
(74) *Attorney, Agent, or Firm* — Harness, Dickey & Pierce, P.L.C.

(57) ABSTRACT

A computer-implemented method is for providing a difference image data record. In an embodiment, the method includes a determination of a first real image data record of an examination volume in respect of a first X-ray energy, and a determination of a multi-energetic real image data record of the examination volume in respect of a first X-ray energy and a second X-ray energy, the second X-ray energy differing from the first X-ray energy. The method further includes the determination of the difference image data record of the examination volume by applying a trained function to input data, wherein the input data is based upon the first real image data record and the multi-energetic real image data record, as well as the provision of the difference image data record.

36 Claims, 10 Drawing Sheets

(52) U.S. Cl.
CPC .... *A61B 6/482* (2013.01); *G06T 2207/10116* (2013.01); *G06T 2207/20081* (2013.01); *G06T 2207/20224* (2013.01); *G06T 2207/30101* (2013.01)

(56) References Cited

U.S. PATENT DOCUMENTS

| | | |
|---|---|---|
| 2013/0046176 A1 | 2/2013 | Mistretta et al. |
| 2017/0123083 A1* | 5/2017 | Divoky ................ G01T 1/2985 |
| 2018/0204357 A1 | 7/2018 | Li et al. |
| 2018/0374209 A1* | 12/2018 | Patil ......................... G06T 7/11 |
| 2020/0013153 A1 | 1/2020 | Kaethner et al. |
| 2020/0226801 A1 | 7/2020 | Kaethner et al. |

OTHER PUBLICATIONS

Ronneberger, Olaf et al. "U-Net: Convolutional Networks for Biomedical Image Segmentation" Medical Image Computing and Computer-Assisted Intervention (MICCAI), Springer, LNCS, vol. 9351, pp. 234-241, 2015 // arXiv:1505.04597 [cs.CV].

Chen, Guang-Hong et al. "Prior image constrained compressed sensing (PICCS): A method to accurately reconstruct dynamic: CT images from highly undersampled projection data sets" Medical Physics, vol. 35, No. 2, pp. 660-663, ISSN: 0094-2405, Feb. 2008 // DOI: 10.1118/1.2836423.

U.S. Office Action for corresponding U.S. Appl. No. 16/736,009 dated Jan. 6, 2022.

A. Elbakri et al.: "Statistical image reconstruction for polyenergetic X-ray computed tomography", IEEE Transactions on Medical Imaging, vol. 21, Nr. 2, pp. 89-99, 2002.

F. Bleichrodt et al.: "SDART: An algorithm for discrete tomography from noisy projections", Computer Vision and Image Understanding 129, pp. 63-74, 2014.

German Office Action for German Application No. DE 102019200269.2 dated Nov. 5, 2019.

Office Action for U.S. Appl. No. 16/736,009 dated Mary 11, 2021.

Office Action for U.S. Appl. No. 16/736,009 dated Aug. 23, 2021.

* cited by examiner

PROVIDING A DIFFERENCE IMAGE DATA RECORD AND PROVIDING A TRAINED FUNCTION

PRIORITY STATEMENT

The present application hereby claims priority under 35 U.S.C. § 119 to German patent application number DE 2019200270.6 filed Jan. 11, 2019, the entire contents of which are hereby incorporated herein by reference.

FIELD

At least one embodiment of the application generally relates to a computer-implemented method for providing a difference image data record and/or providing a trained function.

BACKGROUND

In digital subtraction angiography (DSA for short), one or more vessels are represented in an examination volume by way of X-ray recordings, wherein for the suppression of further structures in the examination volume, recordings of the vessel without contrast medium (so-called mask recordings) are combined with recordings of the vessel including a contrast medium which is situated in the vessel. The contrast medium is introduced into the vessel during the examination in order to determine parameters, in particular hydrodynamic parameters, of a fluid which flows in the vessel.

In four-dimensional DSA, via an image reconstruction method, a time-resolved series of three-dimensional DSA image data is provided. Herein, normalized two-dimensional X-ray projections of an examination volume are back-projected together with time information into a volume element. The two-dimensional X-ray projections usually originate herein from a rotating scan protocol of a C-arm X-ray device.

Since for a digital subtraction angiography, recordings both of the vessel without contrast medium and also of the vessel including a contrast medium are made, the examination volume is exposed to a high X-ray burden. The recordings of the vessel without contrast medium are also known as "mask images".

Hereinafter, an image data record can be denoted a "real image data record" if it reproduces the actual distribution of values and/or intensities (e.g. Hounsfield units, X-ray attenuation coefficients) in an examination volume. An image data record can be denoted a "difference image data record" if it reproduces a difference of an actual distribution of values and/or intensities in an examination volume. However, a difference image data record is not necessarily determined through subtraction of two real image data records. An image data record can be designated a subtraction image data record if it has been determined by subtraction of two image data records, in particular by subtraction of two real image data records. Therefore, in particular, every subtraction image data record could be regarded as a difference image data record, but not every difference image data record can be regarded as a subtraction image data record.

From the unpublished patent application EP18182251, it is known, by applying a trained function to a real image data record, to determine a difference image data record without carrying out an additional mask recording. However, since for example, osseous structures, metal structures (e.g. implants) or calciferous structures (calcification in vessels) in the examination region have a similar X-ray absorption to contrast medium, such structures can lead in the examination region to errors in the determination of the difference image data record.

SUMMARY

At least one embodiment of the present invention achieves a more exact and less error-prone determination of the difference image data record.

Embodiments of the present invention is directed to a method for providing a difference image data record, a method for providing a trained function, a determining system, a training system, via computer program products or computer-readable storage media, according to the claims. Advantageous developments are disclosed in the claims and in the description.

The inventive achievement is described below, both in relation to the claimed devices and also in relation to the claimed method. Features, advantages or alternative embodiments mentioned herein are also transferable similarly to the other claimed subject matter and vice versa. In other words, the present claims (which are directed, for example, to a device) can also be further developed with the features disclosed or claimed in relation to a method. The corresponding functional features of the method are thereby provided by corresponding physical modules.

Furthermore, the inventive achievement is described both in relation to methods and devices for providing difference image data records as well as in relation to methods and devices for providing trained functions. Herein, features and alternative embodiments of data structures and/or functions in methods and devices for providing difference image data records can be transferred to analogous data structures and/or functions in the context of methods and devices for providing trained functions. Herein, analogous data structures can be characterized, in particular, by the use of the qualifier "training". Furthermore, the trained functions used in methods and devices for providing difference image data records can, in particular, have been adapted and/or provided via methods and devices for providing trained functions.

The invention relates in a first embodiment to a computer-implemented method for providing a difference image data record, comprising a determination of a first real image data record of an examination volume in respect of a first X-ray energy, and a determination of a multi-energetic real image data record of the examination volume in respect of a first X-ray energy and a second X-ray energy, wherein the second X-ray energy differs from the first X-ray energy. The method further comprises the determination of the difference image data record of the examination volume by applying a trained function to input data, wherein the input data is based upon the first real image data record and the multi-energetic real image data record, as well as the provision of the difference image data record.

The invention relates in a second embodiment to a computer-implemented method for providing a trained function comprising a determination of a first training real image data record of a training examination volume in respect of a first training X-ray energy, and a determination of a multi-energetic training real image data record of the training examination volume in respect of the first training X-ray energy and a second training X-ray energy, wherein the second training X-ray energy differs from the first training X-ray energy. The method further comprises a determination of a comparison difference image data record of the training examination volume, and a determination of a training difference image data record of the training examination volume by application of the trained function to input data, wherein the input data is based upon the first training real image data record and upon the multi-energetic training real image data record. The method further comprises an adaptation of the trained function based upon a comparison of the training difference image data record and of the comparison difference image data record, as well as a provision of the trained function.

In a third embodiment, the invention relates to a provision system for providing a difference image data record of an examination volume, comprising an interface and a computer unit, wherein the interface and/or the computer unit is configured for determining a first real image data record of the examination volume in respect of a first X-ray energy, wherein the interface and/or the computer unit are further configured for determining a multi-energetic real image data record of the examination volume in respect of the first X-ray energy and a second X-ray energy, wherein the second X-ray energy differs from the first X-ray energy, wherein the computer unit is further configured for determining the difference image data record of the examination volume by application of a trained function to input data, wherein the input data is based upon the first real image data record and the multi-energetic real image data record, and wherein the interface is further configured for providing the difference image data record.

The invention relates in a fourth embodiment to an X-ray device comprising a provision system according to the invention. In particular, the X-ray device comprises a first X-ray source, a second X-ray source, a first X-ray detector and a second X-ray detector. In particular, the first X-ray source and the first X-ray detector are configured to rotate simultaneously around an examination volume. In particular, the second X-ray source and the second X-ray detector are also configured to rotate simultaneously around the examination volume. The X-ray device is, in particular, a dual-source C-arm X-ray system or a dual-source computed tomography system.

In a fifth embodiment, the invention relates to a training system for providing a trained function comprising a training interface and a training computer unit, wherein the training interface and/or the training computer unit are configured for determining a first training real image data record of a training examination volume in respect of a first training X-ray energy, wherein the training interface and/or the training computer unit are further configured for determining a multi-energetic training real image data record of the training examination volume in respect of the first training X-ray energy and a second training X-ray energy, wherein the second training X-ray energy differs from the first training X-ray energy, wherein the training interface and/or the training computer unit are further configured for determining a comparison difference image data record of the training examination volume, wherein the training computer unit is further configured for determining a training difference image data record of the training examination volume by application of the trained function to input data, wherein the input data is based upon the first training real image data record and upon the multi-energetic training real image data record, wherein the training computer unit is further configured for adaptation of the trained function based upon a comparison of the training difference image data record and the comparison difference image data record, wherein the training interface is further configured for providing the trained function.

The invention relates, in a sixth embodiment, to a computer program product having a computer program which is directly loadable into a memory store of a provision system, having program portions in order to carry out all the steps of the method for providing a difference image data record or its embodiments when the program portions are executed by the provision system; and/or which is directly loadable into a training memory store of a training system, having program portions in order to carry out all the steps of the method for providing a trained function or one of its embodiments when the program portions are executed by the training system.

The invention relates, in a possible seventh embodiment, to a computer program product having a computer program which is directly loadable into a memory store of a provision system, having program portions in order to carry out all the steps of the method for providing a difference image data record or its embodiments when the program portions are executed by the provision system.

The invention relates, in a possible eighth embodiment, to a computer program product having a computer program which is directly loadable into a training memory store of a training system, having program portions in order to carry out all the steps of the method for providing a trained function or one of its embodiments when the program portions are executed by the training system.

The invention relates, in a ninth embodiment, to a computer-readable storage medium on which are stored program portions that are readable and executable by a provision system, in order to carry out all the steps of the method for providing a difference image data record or its embodiments when the program portions are executed by the provision system; and/or on which are stored program portions that are readable and executable by a training system, in order to carry out all the steps of the method for providing a trained function or one of its embodiments when the program portions are executed by the training system.

The invention relates, in a possible tenth embodiment, to a computer-readable storage medium on which are stored program portions that are readable and executable by a provision system, in order to carry out all the steps of the method for providing a difference image data record or its embodiments when the program portions are executed by the provision system.

The invention relates, in a possible eleventh embodiment, to a computer-readable storage medium on which are stored program portions that are readable and executable by a training system, in order to carry out all the steps of the method for providing a trained function or one of its embodiments when the program portions are executed by the training system.

The invention relates, in a twelfth embodiment, to a computer program or a computer-readable storage medium comprising a trained function provided through a method for providing a trained function or one of its embodiments.

At least one embodiment of the invention relates to a

At least one embodiment of of the invention relates to a computer-implemented method for providing a trained function, comprising:

determining a first training real image data record of a training examination volume in respect of a first training X-ray energy;

determining a multi-energetic training real image data record of the training examination volume in respect of the first training X-ray energy and a second training X-ray energy, the second training X-ray energy differing from the first training X-ray energy;

determining a comparison difference image data record of the training examination volume;

determining a training difference image data record of the training examination volume by application of the trained function to input data, the input data being based upon the first training real image data record and being based upon the multi-energetic training real image data record;

adapting the trained function based upon a comparison of the training difference image data record and the comparison difference image data record; and providing the trained function.

At least one embodiment of of the invention relates to a provision system for providing a difference image data record of an examination volume, comprising:

an interface; and a computer unit, at least one of the interface and the computer unit being configured to determine a first real image data record of the examination volume in respect of a first X-ray energy, determine a multi-energetic real image data record of the examination volume in respect of the first X-ray energy and a second X-ray energy, the second X-ray energy differing from the first X-ray energy, and determine the difference image data record of the examination volume by application of a trained function to input data, the input data being based upon the first real image data record and the multi-energetic real image data record, and wherein the interface is further configured to provide the difference image data record.

At least one embodiment of of the invention relates to an X-ray device, comprising the provision system of an embodiment.

At least one embodiment of of the invention relates to a training system for providing a trained function, comprising:

a training interface; and a training computer unit, at least one of the training interface and the computer unit being configured to determine a first training real image data record of a training examination volume in respect of a first training X-ray energy, determine a multi-energetic training real image data record of the training examination volume in respect of the first training X-ray energy and a second training X-ray energy, the second training X-ray energy differing from the first training X-ray energy, determine a comparison difference image data record of the training examination volume, and determine a training difference image data record of the training examination volume by application of the trained function to input data, the input data being based upon the first training real image data record and upon the multi-energetic training real image data record, wherein the training computer unit is further configured to adapt the trained function based upon a comparison of the training difference image data record and the comparison difference image data record, and wherein the training interface is further configured to provide the trained function.

At least one embodiment of of the invention relates to a non-transitory computer program product storing a computer program, directly loadable into a memory store of a provision system, including program portions to carry out the method of an embodiment when the program portions are executed by the provision system.

At least one embodiment of of the invention relates to a non-transitory computer-readable storage medium storing program portions, readable and executable by a provision system to carry out the method of an embodiment the program portions are executed by the provision system.

At least one embodiment of of the invention relates to a non-transitory computer-readable storage medium storing program portions, readable and executable by a training system to carry out the method of an embodiment when the program portions are executed by the training system.

BRIEF DESCRIPTION OF THE DRAWINGS

The above-described properties, features and advantages of this invention and the manner in which they are achieved are made more clearly and distinctly intelligible with the following description of the example embodiments which are described in greater detail making reference to the drawings. This description entails no limitation of the invention to these example embodiments. In different figures, the same components are provided with identical reference signs. The figures are in general not to scale. In the drawings.

DETAILED DESCRIPTION OF THE EXAMPLE EMBODIMENTS

Figure 1:
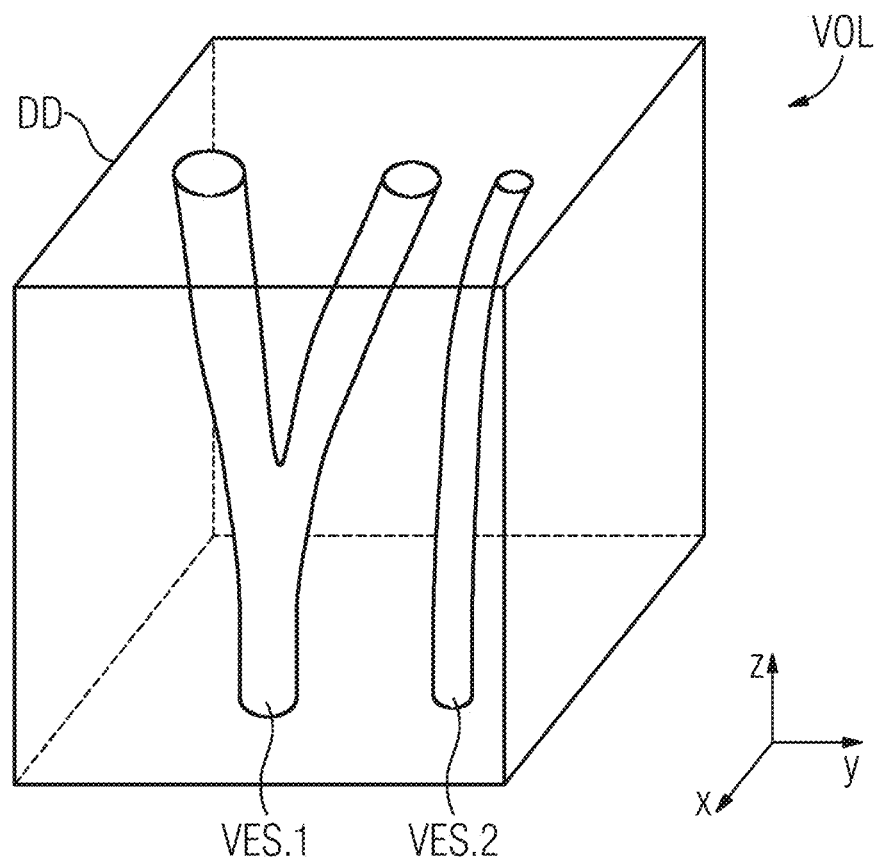
FIG. 1 shows an examination volume with vessels and a three-dimensional difference image data record.

The drawings are to be regarded as being schematic representations and elements illustrated in the drawings are not necessarily shown to scale. Rather, the various elements are represented such that their function and general purpose become apparent to a person skilled in the art. Any connection or coupling between functional blocks, devices, components, or other physical or functional units shown in the drawings or described herein may also be implemented by an indirect connection or coupling. A coupling between components may also be established over a wireless connection. Functional blocks may be implemented in hardware, firmware, software, or a combination thereof.

Various example embodiments will now be described more fully with reference to the accompanying drawings in which only some example embodiments are shown. Specific structural and functional details disclosed herein are merely representative for purposes of describing example embodiments. Example embodiments, however, may be embodied in various different forms, and should not be construed as being limited to only the illustrated embodiments. Rather, the illustrated embodiments are provided as examples so that this disclosure will be thorough and complete, and will fully convey the concepts of this disclosure to those skilled in the art. Accordingly, known processes, elements, and techniques, may not be described with respect to some example embodiments. Unless otherwise noted, like reference characters denote like elements throughout the attached drawings and written description, and thus descriptions will not be repeated. The present invention, however, may be embodied in many alternate forms and should not be construed as limited to only the example embodiments set forth herein.

It will be understood that, although the terms first, second, etc. may be used herein to describe various elements, components, regions, layers, and/or sections, these elements, components, regions, layers, and/or sections, should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items. The phrase "at least one of" has the same meaning as "and/or".

Spatially relative terms, such as "beneath," "below," "lower," "under," "above," "upper," and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below," "beneath," or "under," other elements or features would then be oriented "above" the other elements or features. Thus, the example terms "below" and "under" may encompass both an orientation of above and below. The device may be otherwise oriented (rotated 90 degrees or at other orientations) and the spatially relative descriptors used herein interpreted accordingly. In addition, when an element is referred to as being "between" two elements, the element may be the only element between the two elements, or one or more other intervening elements may be present.

Spatial and functional relationships between elements (for example, between modules) are described using various terms, including "connected," "engaged," "interfaced," and "coupled." Unless explicitly described as being "direct," when a relationship between first and second elements is described in the above disclosure, that relationship encompasses a direct relationship where no other intervening elements are present between the first and second elements, and also an indirect relationship where one or more intervening elements are present (either spatially or functionally) between the first and second elements. In contrast, when an element is referred to as being "directly" connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Expressions such as "at least one of," when preceding a list of elements, modify the entire list of elements and do not modify the individual elements of the list. Also, the term "exemplary" is intended to refer to an example or illustration.

When an element is referred to as being "on," "connected to," "coupled to," or "adjacent to," another element, the element may be directly on, connected to, coupled to, or adjacent to, the other element, or one or more other intervening elements may be present. In contrast, when an element is referred to as being "directly on," "directly connected to," "directly coupled to," or "immediately adjacent to," another element there are no intervening elements present.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Before discussing example embodiments in more detail, it is noted that some example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Specific structural and functional details disclosed herein are merely representative for purposes of describing example embodiments of the present invention. This invention may, however, be embodied in many alternate forms and should not be construed as limited to only the embodiments set forth herein.

Units and/or devices according to one or more example embodiments may be implemented using hardware, software, and/or a combination thereof. For example, hardware devices may be implemented using processing circuity such as, but not limited to, a processor, Central Processing Unit (CPU), a controller, an arithmetic logic unit (ALU), a digital signal processor, a microcomputer, a field programmable gate array (FPGA), a System-on-Chip (SoC), a programmable logic unit, a microprocessor, or any other device capable of responding to and executing instructions in a defined manner. Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/hardware, that manipulates and transforms data represented as physical, electronic quantities within the computer system's registers and memories into other data similarly represented as physical quantities within the computer system memories or registers or other such information storage, transmission or display devices.

In this application, including the definitions below, the term 'module' or the term 'controller' may be replaced with the term 'circuit.' The term 'module' may refer to, be part of, or include processor hardware (shared, dedicated, or group) that executes code and memory hardware (shared, dedicated, or group) that stores code executed by the processor hardware.

The module may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

Software may include a computer program, program code, instructions, or some combination thereof, for independently or collectively instructing or configuring a hardware device to operate as desired. The computer program and/or program code may include program or computer-readable instructions, software components, software modules, data files, data structures, and/or the like, capable of being implemented by one or more hardware devices, such as one or more of the hardware devices mentioned above. Examples of program code include both machine code produced by a compiler and higher level program code that is executed using an interpreter.

For example, when a hardware device is a computer processing device (e.g., a processor, Central Processing Unit (CPU), a controller, an arithmetic logic unit (ALU), a digital signal processor, a microcomputer, a microprocessor, etc.), the computer processing device may be configured to carry out program code by performing arithmetical, logical, and input/output operations, according to the program code. Once the program code is loaded into a computer processing device, the computer processing device may be programmed to perform the program code, thereby transforming the computer processing device into a special purpose computer processing device. In a more specific example, when the program code is loaded into a processor, the processor becomes programmed to perform the program code and operations corresponding thereto, thereby transforming the processor into a special purpose processor.

Software and/or data may be embodied permanently or temporarily in any type of machine, component, physical or virtual equipment, or computer storage medium or device, capable of providing instructions or data to, or being interpreted by, a hardware device. The software also may be distributed over network coupled computer systems so that the software is stored and executed in a distributed fashion. In particular, for example, software and data may be stored by one or more computer readable recording mediums, including the tangible or non-transitory computer-readable storage media discussed herein.

Even further, any of the disclosed methods may be embodied in the form of a program or software. The program or software may be stored on a non-transitory computer readable medium and is adapted to perform any one of the aforementioned methods when run on a computer device (a device including a processor). Thus, the non-transitory, tangible computer readable medium, is adapted to store information and is adapted to interact with a data processing facility or computer device to execute the program of any of the above mentioned embodiments and/or to perform the method of any of the above mentioned embodiments.

Example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order.

According to one or more example embodiments, computer processing devices may be described as including various functional units that perform various operations and/or functions to increase the clarity of the description. However, computer processing devices are not intended to be limited to these functional units. For example, in one or more example embodiments, the various operations and/or functions of the functional units may be performed by other ones of the functional units. Further, the computer processing devices may perform the operations and/or functions of the various functional units without sub-dividing the operations and/or functions of the computer processing units into these various functional units.

Units and/or devices according to one or more example embodiments may also include one or more storage devices. The one or more storage devices may be tangible or non-transitory computer-readable storage media, such as random access memory (RAM), read only memory (ROM), a permanent mass storage device (such as a disk drive), solid state (e.g., NAND flash) device, and/or any other like data storage mechanism capable of storing and recording data. The one or more storage devices may be configured to store computer programs, program code, instructions, or some combination thereof, for one or more operating systems and/or for implementing the example embodiments described herein. The computer programs, program code, instructions, or some combination thereof, may also be loaded from a separate computer readable storage medium into the one or more storage devices and/or one or more computer processing devices using a drive mechanism. Such separate computer readable storage medium may include a Universal Serial Bus (USB) flash drive, a memory stick, a Blu-ray/DVD/CD-ROM drive, a memory card, and/or other like computer readable storage media. The computer programs, program code, instructions, or some combination thereof, may be loaded into the one or more storage devices and/or the one or more computer processing devices from a remote data storage device via a network interface, rather than via a local computer readable storage medium. Additionally, the computer programs, program code, instructions, or some combination thereof, may be loaded into the one or more storage devices and/or the one or more processors from a remote computing system that is configured to transfer and/or distribute the computer programs, program code, instructions, or some combination thereof, over a network. The remote computing system may transfer and/or distribute the computer programs, program code, instructions, or some combination thereof, via a wired interface, an air interface, and/or any other like medium.

The one or more hardware devices, the one or more storage devices, and/or the computer programs, program code, instructions, or some combination thereof, may be specially designed and constructed for the purposes of the example embodiments, or they may be known devices that are altered and/or modified for the purposes of example embodiments.

A hardware device, such as a computer processing device, may run an operating system (OS) and one or more software applications that run on the OS. The computer processing device also may access, store, manipulate, process, and create data in response to execution of the software. For simplicity, one or more example embodiments may be exemplified as a computer processing device or processor; however, one skilled in the art will appreciate that a hardware device may include multiple processing elements or processors and multiple types of processing elements or processors. For example, a hardware device may include multiple processors or a processor and a controller. In addition, other processing configurations are possible, such as parallel processors.

The computer programs include processor-executable instructions that are stored on at least one non-transitory computer-readable medium (memory). The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc. As such, the one or more processors may be configured to execute the processor executable instructions.

The computer programs may include: (i) descriptive text to be parsed, such as HTML (hypertext markup language) or XML (extensible markup language), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C#, Objective-C, Haskell, Go, SQL, R, Lisp, Java®, Fortran, Perl, Pascal, Curl, OCaml, Javascript®, HTML5, Ada, ASP (active server pages), PHP, Scala, Eiffel, Smalltalk, Erlang, Ruby, Flash®, Visual Basic®, Lua, and Python®.

Further, at least one embodiment of the invention relates to the non-transitory computer-readable storage medium including electronically readable control information (processor executable instructions) stored thereon, configured in such that when the storage medium is used in a controller of a device, at least one embodiment of the method may be carried out.

The computer readable medium or storage medium may be a built-in medium installed inside a computer device main body or a removable medium arranged so that it can be separated from the computer device main body. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

Although described with reference to specific examples and drawings, modifications, additions and substitutions of example embodiments may be variously made according to the description by those of ordinary skill in the art. For example, the described techniques may be performed in an order different with that of the methods described, and/or components such as the described system, architecture, devices, circuit, and the like, may be connected or combined to be different from the above-described methods, or results may be appropriately achieved by other components or equivalents.

The invention relates in a first embodiment to a computer-implemented method for providing a difference image data record, comprising a determination of a first real image data record of an examination volume in respect of a first X-ray energy, and a determination of a multi-energetic real image data record of the examination volume in respect of a first X-ray energy and a second X-ray energy, wherein the second X-ray energy differs from the first X-ray energy. The method further comprises the determination of the difference image data record of the examination volume by applying a trained function to input data, wherein the input data is based upon the first real image data record and the multi-energetic real image data record, as well as the provision of the difference image data record.

The determination of the first real image data record can herein be carried out in that the first real image data record is received. Furthermore, the determination of the multi-energetic real image data record can herein be carried out in that the multi-energetic real image data record is received. The determination of the first real image data record can herein take place, in particular, via an interface and/or a computer unit. The determination of the difference image data record can herein take place, in particular, via the computer unit. The provision of the difference image data record can herein take place, in particular, via the interface. The provision of the difference image data record can herein comprise, in particular, a storage, a transference and/or a display of a difference image data record.

The first and second X-ray energy correspond herein to the accelerating voltage of an X-ray tube or the energy of an X-ray photon. In particular, the expressions "first X-ray energy" and "second X-ray energy" also denote a first X-ray spectrum and a second X-ray spectrum, wherein an X-ray spectrum corresponds to an intensity distribution of the different wavelengths or energies of X-ray radiation. In particular, X-ray radiation, the accelerating voltage used for generating it, its energy or its spectrum correspond to an X-ray energy, is characterized by this X-ray energy.

An image data record comprises, in particular, a plurality of pixels or voxels. An intensity value is thereby assigned to each pixel or voxel. In an X-ray image data record, in particular, each pixel or voxel is assigned an X-ray intensity value which is a measure for the X-ray intensity incident in this pixel or voxel or for an X-ray absorption coefficient of the pixel or the voxel. An incident X-ray intensity depends upon the number, the size, the shape and the material of the object located in the examination volume and penetrated by the X-ray radiation. An image data record can comprise, in particular, further data, in particular, metadata of an imaging examination, in particular, of an X-ray examination.

A two-dimensional image data record herein comprises at least one two-dimensional representation of an examination volume. A three-dimensional image data record herein comprises at least one three-dimensional representation of an examination volume, and in particular, a three-dimensional image data record can also additionally comprise one or more two-dimensional representations of the examination volume.

A real image data record of the examination volume in respect of an X-ray energy can be an X-ray image data record of the examination volume which has been recorded with X-ray radiation having this X-ray energy. A real image data record of the examination volume in respect of an X-ray energy can also be based upon an X-ray image data record of the examination volume which has been recorded with X-ray radiation having this X-ray energy. A multi-energetic real image data record of the examination volume in respect of a first X-ray energy and a second X-ray energy can comprise an X-ray image data record of the examination volume which has been recorded via X-ray radiation characterized by the first X-ray energy, and an X-ray image data record of the examination volume which has been recorded via X-ray radiation characterized by the second X-ray energy. A multi-energetic real image data record of the examination volume can also be based upon an X-ray energy image data record of the examination volume which has been recorded via X-ray radiation characterized by the first X-ray energy, and upon an X-ray image data record of the examination volume which has been recorded via X-ray radiation characterized by the second X-ray energy.

A trained function maps input data onto output data. For this purpose, the output data can in particular further depend upon one or more parameters of the trained function. The one or more parameters of the trained function can be determined and/or adapted by training. The determination and/or the adaptation of the one or more parameters of the trained function can be based, in particular, upon a pair made from training input data and associated training output data, wherein the trained function is applied to the training input data for generating training imaging data. In particular, the determination and/or the adaptation can be based upon a comparison of the training imaging data and the training output data. In general, a trainable function, that is, a function with not yet adapted, one or a plurality of parameters, can be designated a trained function.

Other expressions for a trained function are trained imaging rule, imaging rule with trained parameters, function with trained parameters, algorithm based upon artificial intelligence, machine learning algorithm. A further example of a trained function is an artificial neural network wherein the edge weights of the artificial neural network correspond to the parameters of the trained function. In place of the expression "neural network", the expression "neural net" can also be used. In particular, a trained function can also be a "deep neural network" (or "deep artificial neural network"). An example of a trained function is a "support vector machine" and furthermore, in particular, other machine learning algorithms are usable as a trained function.

In particular, the first real image data record and the multi-energetic real image data record have the same dimension. In particular, the first real image data record is a two-dimensional image data record, a three-dimensional or a four-dimensional image data record.

In particular, the first real image data record and the multi-energetic real image data record image the examination volume, in other words, the image region of the first real image data record corresponds to the image region of the multi-energetic real image data record. In particular, the multi-energetic real image data record has a higher spatial resolution than the first real image data record. In particular, the spatial extent of the multi-energetic real image data record measured in pixels or voxels is greater in respect of at least one dimension than the spatial extent of the first real image data record measured in pixels or voxels.

In particular, the multi-energetic real image data record and the difference image data record have the same dimension. In particular therefore, the difference image data record is a two-dimensional, a three-dimensional or a four-dimensional image data record.

In particular, the multi-energetic real image data record and the difference image data record map the examination volume, in other words, the image region of the multi-energetic real image data record corresponds to the image region of the difference image data record. In particular, the multi-energetic real image data record and the difference image data record have the same spatial resolution. In particular, the spatial extent of the multi-energetic real image data record measured in pixels or voxels is the same in respect of each of the dimensions as the spatial extent of the difference image data record measured in pixels or voxels.

The inventors have identified that through the use both of a first real image data record as well as a multi-energetic real image data record, the properties of the examination volume can be made available more exactly as input data for the trained function. In particular, through the use of a first and a second X-ray energy, it is possible to distinguish between materials which have similar X-ray absorption values at one of the two X-ray energies and thus cannot or can only poorly be distinguished on use of only one X-ray energy. Thus, by way of the trained function, in particular, better distinguishing between different materials in the examination region can be achieved, and a more exact and, in particular, less error-prone difference image data record can be determined.

The inventors have also identified that a high resolution of the multi-energetic real image data record is sufficient for achieving a corresponding resolution of the difference image data record. The distinguishing of different materials based upon the different X-ray energies can take place based upon the first real image data record with a lower resolution. For the improved distinguishing, it is therefore, in particular, not necessary to expose the examination volume to a larger X-ray dose, since a lower resolution of the first real image data record and consequently less raw data is sufficient for the first real image data record.

According to a further embodiment of the invention, the method for determining a difference image data record further comprises the determination of a second real image data record of the examination volume in respect of a second X-ray energy, wherein the input data is further based upon the second real image data record.

The determination of the second real image data record can herein be carried out in that the second real image data record is received. The determination of the second real image data record can herein take place, in particular, via an interface and/or a computer unit.

In particular, the second real image data record and the multi-energetic real image data record have the same dimension. In particular, the second real image data record is a two-dimensional image data record, a three-dimensional or a four-dimensional image data record.

In particular, the second real image data record and the multi-energetic real image data record map the examination volume, in other words, the image region of the second real image data record corresponds to the image region of the multi-energetic real image data record. In particular, the multi-energetic real image data record has a higher spatial resolution than the first real image data record. In particular, the spatial extent of the multi-energetic real image data record measured in pixels or voxels is greater in respect of at least one dimension than the spatial extent of the first real image data record measured in pixels or voxels.

The inventors have identified that by the use of the second real image data record in the input data, an improved distinction between different materials in the examination region can be achieved since, thereby, information regarding the X-ray absorption of regions of the examination volume in respect of the second X-ray energy alone is also present and can be processed.

According to another possible embodiment of the invention, the first real image data record is based upon first output data and the multi-energetic real image data record is based upon the first and second output data in respect of the second X-ray energy. In particular, the spatial resolution of the multi-energetic real image data record is higher than the spatial resolution of the first real image data record. In particular, the spatial resolution of the multi-energetic real image data record is identical to the resolution of the difference image data record. According to another possible embodiment of the invention, the second real image data record is based upon the second output data. In particular, the spatial resolution of the multi-energetic real image data record is higher than the spatial resolution of the second real image data record.

The inventors have identified that under the condition that the first real image data record is based upon first output data, the optional second real image data record is based upon second output data, but the multi-energetic real image data record is based upon the first and the second output data, it is not necessary as compared with the prior art to expose the examination volume to a higher X-ray dose. This also applies if a second real image data record is used. The spatial resolution of the difference image data record can specifically be based upon the multi-energetic real image data record and the X-ray energy-dependent differentiation between different materials can then take place based upon lower-resolution first and second real image data records.

According to a further embodiment of the invention, the method for determining a difference image data record further comprises the reception of first X-ray projections of the examination volume in respect of the first X-ray energy and the reception of second X-ray projections of the examination volume in respect of the second X-ray energy; wherein the first real image data record is based upon and/or comprises the first X-ray projections; and/or wherein the second real image data record is based upon and/or comprises the second X-ray projections; and/or wherein the multi-energetic real image data record is based upon and/or comprises the first X-ray projections and the second X-ray projections.

The reception of the first X-ray projections can be carried out, in particular, via the interface. The reception of the second X-ray projections can be carried out, in particular, via the interface. In particular, the first X-ray projections correspond to the first output data and the second X-ray projections correspond to the second output data.

A first X-ray projection in respect of a first X-ray energy is, in particular, an X-ray projection which has been recorded with X-ray radiation of the first X-ray energy. A second X-ray projection in respect of a second X-ray energy is, in particular, an X-ray projection which has been recorded with X-ray radiation of the second X-ray energy.

The inventors have identified that by the use of a plurality of two-dimensional X-ray projections, in particular, changes in the examination volume over time can also be taken into account, in particular, a changing contrast medium concentration over time. By this means, the trained function can determine the difference image data record with more data and therefore, in particular, also more exactly and less prone to error.

According to a further embodiment of the invention, the first real image data record is an at least three-dimensional reconstruction of the first X-ray projections; and/or the second real image data record is an at least three-dimensional reconstruction of the second X-ray projections; and/or the multi-energetic real image data record is an at least three-dimensional reconstruction of the first X-ray projections and of the second X-ray projections. In particular, the reconstruction of the first X-ray projections and of the second X-ray projections is independent of the first X-ray energy and the second X-ray energy and/or the reconstruction is a reconstruction without taking account of the X-ray energy.

In general, a reconstruction denotes the determination of an n-dimensional image data record based upon a plurality of m-dimensional image data records, wherein m<n. Herein, the plurality of m-dimensional image data records are, in particular, projections of an n-dimensional volume which is to be described by way of the n-dimensional image data record. In particular, a reconstruction can denote the determination of a three-dimensional image data record based upon a plurality of two-dimensional image data records. Such a reconstruction can be based, for example, on a filtered back-projection, or alternatively, iterative reconstruction methods or the Feldkamp algorithm are known to a person skilled in the art.

The inventors have identified that three-dimensional real image data records are particularly suitable for representing the properties of the examination volume. In particular, by way of three-dimensional real image data records, almost complete information regarding the examination volume can be acquired.

According to a further embodiment of the invention, the method for determining a difference image data record further comprises the reception of first X-ray projections of the examination volume in respect of the first X-ray energy, wherein the first real image data record is based upon and/or comprises the first X-ray projections. As distinct from the embodiments described above, in this embodiment of the invention, second X-ray projections do not necessarily have to be received.

According to a further embodiment of the invention, during the recording of the first X-ray projections, the examination volume comprises contrast medium and/or during the recording of the second X-ray projections, the examination volume comprises contrast medium. In particular, the examination volume comprises contrast medium if one or more vessels in the examination volume contain contrast medium. In particular, the concentration of the contrast medium is variable over time. The inventors have identified that the trained function can extract vessel structures particularly well if these are emphasized by the presence of contrast medium.

According to a further embodiment of the invention, the first X-ray projections and the second X-ray projections were recorded simultaneously. Herein, the first X-ray projections and the second X-ray projections are designated simultaneously recorded if the first X-ray projections and the second X-ray projections were recorded within a time interval of 30 s or less, in particular within a time interval of 20 s or less, in particular within a time interval of 10 s or less, in particular within a time interval of 5 s or less.

The inventors have identified that with simultaneous recording of the first and second X-ray projections, they each map the same or a similar temporal state of the examination volume. By this means, the first real image data record and the second real image data record and/or the multi-energetic real image data record also describe the same or a similar state of the examination volume and by way of this state, information in respect of both the first and also the second X-ray energy is available.

According to a further embodiment of the invention, the first X-ray projections are recordings of a first X-ray source and a first X-ray detector and the second X-ray projections are recordings of a second X-ray source and a second X-ray detector.

In particular, the first X-ray source differs from the second X-ray source, and in particular, the second X-ray detector differs from the first X-ray detector. In particular, the first and the second X-ray source have the same construction and/or the same type, and/or the first X-ray detector and the second X-ray detector have the same construction and/or the same type.

The inventors have identified that via two X-ray sources and via two X-ray detectors, the first X-ray projections and the second X-ray projections can be recorded independently of one another. In particular, thereby, necessary movements between recordings of the first X-ray projections and the second X-ray projections can be reduced, in particular if the first X-ray projections and the second X-ray projections are recorded alternatingly. Furthermore, thereby, the first X-ray source can be operated with the first X-ray energy and the second X-ray source can be operated with the second X-ray energy, so that switching processes between the first and the second X-ray energy can be dispensed with.

According to a further embodiment of the invention, a biplanar X-ray device comprises the first X-ray source, the second X-ray source, the first X-ray detector and the second X-ray detector. The inventors have identified that by using a biplanar X-ray device, the first X-ray source and the first X-ray detector can be better coordinated with the second X-ray source and the second X-ray detector. In particular, a registration of the first X-ray source and of the first X-ray detector in respect of the first X-ray source and the second X-ray detector can be dispensed with since the relative positions of the X-ray sources and the X-ray detectors in a biplanar X-ray device are known.

According to a further embodiment of the invention, each of the first X-ray projections is an X-ray projection of the examination volume in respect of a projection direction from a first projection angle region and each of the second X-ray projections is an X-ray projection of the examination volume in respect of a projection direction from a second projection angle region, wherein the first projection angle region and the second projection angle region differ.

The projection direction of an X-ray projection is, in particular, the direction from the position of an X-ray source to the position of an X-ray detector at the time point of the recording of the X-ray projection, wherein the X-ray projection has been recorded via the X-ray source and via the X-ray detector. A projection direction can be regarded, in particular, as a vector or as a straight line in space.

A projection angle region comprises a plurality of projection directions. In particular, the projection angle region can also be regarded as a solid angle region in respect of a point of the examination volume, in particular, in respect of the middle point of the examination volume. In particular, in this case, the plurality of projection directions in respect of the point of the examination volume lies in this solid angle region. Alternatively, the projection angle region can also be regarded as a locus curve of an X-ray detector on recording X-ray projections. In particular, the projection angle region can also be regarded as a circular arc. In particular, the projection angle region can also be regarded as a convex envelope of the plurality of projection directions.

The inventors have identified that (under the assumption that the first projection angle region and the second projection angle region have a fixed size) first and second X-ray projections from different projection angle regions contain more spatial information regarding the examination region than from the same projection angle regions. Herein, the better spatial information can relate both to the size of the angular region covered and also to the angular resolution.

According to a further embodiment of the invention, the first projection angle region and the second projection angle region are disjoint. The first projection angle region and the second projection angle region are, in particular, disjoint if no projection direction of the first projection angle region is included in the second projection angle region and if no projection direction of the second projection angle region is included in the first projection angle region.

The inventors have identified that by way of disjoint projection angle regions, a particularly large angular region can be covered.

According to a further embodiment of the invention, the first projection angle region includes the second projection angle region or the second projection angle region includes the first projection angle region. The inventors have identified that through the use of overlapping projection angle regions both for the first and also for the second X-ray energy, a complete angular information is available, and therefore, in particular, for the entire angular region, by way of the trained function, it is possible to differentiate between different materials.

According to a further embodiment of the invention, the output data of the trained function comprises a probability data record, wherein the difference image data record is based upon the probability data record.

The probability data record herein assigns a probability value, in particular, to one or more pixels or voxels of the multi-energetic real image data record. In particular, the probability value can assign to all pixels or voxels of the multi-energetic real image data record a probability value and, in this case, the probability data record can be regarded as a probability image data record. A probability value is, in particular, a number greater than or equal to 0 and smaller than or equal to 1. The probability value assigned to a voxel can relate, in particular, to the probability that the voxel is contained in the image of a vessel situated in the examination volume. Alternatively, the probability value assigned to a voxel can relate, in particular, to the probability that the voxel is not contained in a mapping of a vessel situated in the examination volume.

A probability value can also, in particular, be binary, i.e. it can either have the value 0 or the value 1. In this case, the probability image data record can also be regarded as a segmentation of the multi-energetic real image data record, in particular, as a segmentation of the image of a vessel in the multi-energetic real image data record.

The probability data record has herein, in particular, the same dimension as the multi-energetic real image data record and/or the difference image data record. Furthermore, the probability data record has, in particular, in respect of each dimension, the same extent as the multi-energetic real image data record and/or the difference image data record, wherein the extent is measured, in particular, in the number of pixels or the number of voxels.

The inventors have identified that, in the application of the trained function to the input data, probability values can be particularly easily determined therefor in that particular voxels of the multi-energetic real image data record correspond to a vessel contained within the examination volume. In a wider sense, this involves an image processing wherein trained functions can achieve good results for image processing in a known manner.

According to a further embodiment of the invention, the method for determining a difference image data record comprises, in particular, the reception of a transfer function and the modification of the probability data record based upon the transfer function.

The reception of the transfer function herein takes place, in particular, with the interface, while the modification of the probability data record is herein carried out, in particular, via the computer unit.

A transfer function is, in particular, a function which maps probability values onto probability values. In particular, therefore, a transfer function is a function that maps the interval $[0; 1]$ onto the interval $[0; 1]$. In particular, the transfer function T can be a monotonically increasing function, i.e. $T(x) \leq T(y)$ for $x < y$, in particular, the transfer function T can also be a strictly monotonically increasing function, i.e. $T(x) < T(y)$ for $x < y$. Advantageously, the transfer function is a continuous function or a differentiable function. Advantageously the relations $T(0)=0$ and $T(1)=1$ apply for the transfer function T.

The transfer function can be specified, in particular, by a user. Alternatively, the transfer function can also be selected from a plurality of available transfer functions, for example, based upon the type of the real image data record, based upon recording parameters for the first, the second and/or the multi-energetic real image data record or for the first and/or second X-ray projections, based upon the position of the examination volume in the body of the patient and/or based upon a vessel contained within the examination volume.

The modification of the probability data record can comprise, in particular, an application of the transfer function to each probability value of the probability data record. In particular, for each probability value of the probability data record, a modified probability value is determined in that the transfer function is applied to the probability value and, in particular, the modified probability data record comprises the modified probability values.

The inventors have identified that through the application of a suitable transfer function, image structures or the intensity of image structures that correspond to the background can be increased or lessened. If, for example $T(x)=x^\gamma$ is used as the transfer function, then for $0<\gamma<1$ image structures which correspond to the background are intensified, and for $\gamma>1$, image structures which correspond to the background are weakened.

According to a further embodiment of the invention, the difference image data record is based upon a multiplication of the probability data record by the first real image data record and/or by the second real image data record and/or by the multi-energetic real image data record. In particular, the difference image data record corresponds to a multiplication of the probability data record by the multi-energetic real image data record.

The inventors have identified that by way of the multiplication of the probability data record by one of the real image data records, a three-dimensional difference image data record can be generated efficiently since the intensity values of image regions with low probability values are removed through the multiplication, and these image regions correspond to the very regions of the examination volume which do not correspond to the vessels contained within the examination volume.

In a possible further embodiment, the invention relates to a method for determining a difference image data record of an examination volume, comprising: receiving two-dimensional first X-ray projections of an examination volume in respect of a first X-ray energy; receiving two-dimensional second X-ray projections of the examination volume in respect of a second X-ray energy, wherein the first and the second X-ray energy differ; determining a three-dimensional first real image data record based upon the two-dimensional first X-ray projections; determining a three-dimensional multi-energetic real image data record based upon the two-dimensional first X-ray projections and on the two-dimensional second X-ray projections; determining a difference image data record through the application of a trained function to input data, wherein the input data comprises the three-dimensional first real image data record and the three-dimensional multi-energetic real image data record; and providing the three-dimensional difference image data record.

The invention relates in a second embodiment to a computer-implemented method for providing a trained function comprising a determination of a first training real image data record of a training examination volume in respect of a first training X-ray energy, and a determination of a multi-energetic training real image data record of the training examination volume in respect of the first training X-ray energy and a second training X-ray energy, wherein the second training X-ray energy differs from the first training X-ray energy. The method further comprises a determination of a comparison difference image data record of the training examination volume, and a determination of a training difference image data record of the training examination volume by application of the trained function to input data, wherein the input data is based upon the first training real image data record and upon the multi-energetic training real image data record. The method further comprises an adaptation of the trained function based upon a comparison of the training difference image data record and of the comparison difference image data record, as well as a provision of the trained function.

The determination of the first training real image data record can herein take place in that the first training real image data record is received. The determination of the multi-energetic training real image data record can herein take place in that the multi-energetic training real image data record is received. The determination of the comparison difference image data record can herein take place in that the comparison difference image data record is received. The provision of the trained function can, in particular, take place in that the trained function is displayed, transferred and/or stored.

In particular, the determination of the first training real image data record can take place via a training interface and/or via a training computer unit. In particular, the determination of the multi-energetic training real image data record can take place via the training interface and/or via the training computer unit. In particular, the determination of the comparison difference image data record can take place via the training interface and/or via the training computer unit. In particular, the determination of the training difference image data record can take place via the training computer unit. In particular, the adaptation of the trained function can take place via the training computer unit. In particular, the provision of the trained function can take place via the training interface.

The first training real image data record can comprise, in particular, all the properties of the first real image data record which have been described in relation to the method for providing a difference image data record. In particular, the first training real image data record is a real image data record. The multi-energetic training real image data record can comprise, in particular, all the properties of the multi-energetic real image data record which have been described in relation to the method for providing a difference image data record. In particular, the multi-energetic training real image data record is a real image data record. A training difference image data record and a comparison difference image data record can comprise all the properties of the difference image data record which have been described in relation to the method for providing a difference image data record.

The inventors have identified that with the method described, a trained function can be provided which can be used in the method for providing a difference image data record.

According to a further possible embodiment of the invention, the method for providing a trained function further comprises a determination of a second training real image data record of the training examination volume in respect of the second training X-ray energy, wherein the input data is further based upon the second training real image data record. The determination of the second training real image data record can herein take place in that the second training real image data record is received. The determination of the second training real image data record, in particular, can take place via the training interface and/or via the training computer unit. The second training real image data record can comprise, in particular, all the properties of the second real image data record which have been described in relation to the method for providing a difference image data record. In particular, the second training real image data record is a real image data record.

According to a further embodiment of the invention, the method for providing a trained function comprises a determination of a mask image data record of the training examination volume, wherein the comparison difference image data record is determined by way of a digital subtraction angiography based upon the mask image data record and the first training real image data record or by way of a digital subtraction angiography based upon the mask image data record and the multi-energetic training real image data record. In particular, the comparison difference image data record can also be determined by way of a digital subtraction angiography based upon the mask image data record and the second training real image data record.

The determination of the mask image data record can take place, in particular, by way of a reception of the mask image data record. Alternatively, the determination of the mask image data record can also take place based upon mask X-ray projections of the training examination volume, wherein the training examination volume contains no contrast medium at the time point of the recording of the mask X-ray projections. The determination of the mask image data record can take place, in particular, via the training interface and/or via the training computer unit.

In particular, the comparison difference image data record can take place by way of a subtraction of the multi-energetic training real image data record and of the mask image data record. In this case, the comparison difference image data record is, in particular, a subtraction image data record.

The inventors have identified that by way of the comparison of the training difference image data record with a comparison difference image data record, wherein the comparison difference image data record is based upon a digital subtraction angiography, the output data of the trained function corresponds particularly well to the results of a digital subtraction angiography. In particular, the output data of the trained function can be used in place of results of a digital subtraction angiography.

According to a further embodiment of the invention, the method for providing a trained function further comprises a reception of a first three-dimensional material model of the training examination volume, wherein the first training real image data record and/or the multi-energetic training real image data record is based upon a simulation of an interaction between X-ray radiation and the first three-dimensional material model.

A material model assigns, in particular, a material property to a set of spatial locations. The spatial locations can be defined, in particular, by voxels. A material property can be, in particular, an X-ray absorption coefficient or a function which defines the X-ray absorption coefficient dependent upon the X-ray energy.

A training real image data record can be simulated, in particular, in that the interaction of X-ray radiation of the first X-ray energy and/or of the second X-ray energy in respect of a projection direction is simulated with the spatial distribution of the material properties. The simulation can take place, in particular, by way of a Monte Carlo simulation.

The inventors have identified that by using a material model for the adaptation of the parameters of the trained function, the recording of actual image data can largely be dispensed with. By this means, any desired number of training data can be generated without exposing patients to an unnecessary radiation dose through X-ray recordings.

According to a further embodiment of the invention, the method for providing a trained function further comprises a reception of a second three-dimensional material model of the training examination volume, wherein the first three-dimensional material model is a material model of the training examination volume including contrast medium, wherein the second three-dimensional material model is a material model of the training examination volume without contrast medium, and wherein the mask image data record is based upon a simulation of an interaction between X-ray radiation and the second three-dimensional material model.

The inventors have identified that by using a first material model with contrast medium and a second material model without contrast medium, a digital subtraction angiography can be completely described. By this means, without recording real training data, training data can be generated for the trained function by simulation. In particular, by this means, a comparison difference image data record can be determined as the difference of the mask image data record and the training difference image data record without recording real training data or exposing patients to a radiation burden.

In a third embodiment, the invention relates to a provision system for providing a difference image data record of an examination volume, comprising an interface and a computer unit, wherein the interface and/or the computer unit is configured for determining a first real image data record of the examination volume in respect of a first X-ray energy, wherein the interface and/or the computer unit are further configured for determining a multi-energetic real image data record of the examination volume in respect of the first X-ray energy and a second X-ray energy, wherein the second X-ray energy differs from the first X-ray energy, wherein the computer unit is further configured for determining the difference image data record of the examination volume by application of a trained function to input data, wherein the input data is based upon the first real image data record and the multi-energetic real image data record, and wherein the interface is further configured for providing the difference image data record.

Such a provision unit can be configured, in particular, to carry out the previously described inventive method for providing a difference image data record and its embodiments. The provision unit is configured to carry out this method and its embodiments in that the interface and the computer unit are configured to carry out the corresponding method steps.

The invention relates in a fourth embodiment to an X-ray device comprising a provision system according to the invention. In particular, the X-ray device comprises a first X-ray source, a second X-ray source, a first X-ray detector and a second X-ray detector. In particular, the first X-ray source and the first X-ray detector are configured to rotate simultaneously around an examination volume. In particular, the second X-ray source and the second X-ray detector are also configured to rotate simultaneously around the examination volume. The X-ray device is, in particular, a dual-source C-arm X-ray system or a dual-source computed tomography system.

In a fifth embodiment, the invention relates to a training system for providing a trained function comprising a training interface and a training computer unit, wherein the training interface and/or the training computer unit are configured for determining a first training real image data record of a training examination volume in respect of a first training X-ray energy, wherein the training interface and/or the training computer unit are further configured for determining a multi-energetic training real image data record of the training examination volume in respect of the first training X-ray energy and a second training X-ray energy, wherein the second training X-ray energy differs from the first training X-ray energy, wherein the training interface and/or the training computer unit are further configured for determining a comparison difference image data record of the training examination volume, wherein the training computer unit is further configured for determining a training difference image data record of the training examination volume by application of the trained function to input data, wherein the input data is based upon the first training real image data record and upon the multi-energetic training real image data record, wherein the training computer unit is further configured for adaptation of the trained function based upon a comparison of the training difference image data record and the comparison difference image data record, wherein the training interface is further configured for providing the trained function.

Such a training system can be configured, in particular, to carry out the previously described inventive method for providing a trained function, and its embodiments. The training system is configured to carry out this method and its embodiments in that the training interface and the training computer unit are configured to carry out the corresponding method steps.

The invention relates, in a sixth embodiment, to a computer program product having a computer program which is directly loadable into a memory store of a provision system, having program portions in order to carry out all the steps of the method for providing a difference image data record or its embodiments when the program portions are executed by the provision system; and/or which is directly loadable into a training memory store of a training system, having program portions in order to carry out all the steps of the method for providing a trained function or one of its embodiments when the program portions are executed by the training system.

The invention relates, in a possible seventh embodiment, to a computer program product having a computer program which is directly loadable into a memory store of a provision system, having program portions in order to carry out all the steps of the method for providing a difference image data record or its embodiments when the program portions are executed by the provision system.

The invention relates, in a possible eighth embodiment, to a computer program product having a computer program which is directly loadable into a training memory store of a training system, having program portions in order to carry out all the steps of the method for providing a trained function or one of its embodiments when the program portions are executed by the training system.

The invention relates, in a ninth embodiment, to a computer-readable storage medium on which are stored program portions that are readable and executable by a provision system, in order to carry out all the steps of the method for providing a difference image data record or its embodiments when the program portions are executed by the provision system; and/or on which are stored program portions that are readable and executable by a training system, in order to carry out all the steps of the method for providing a trained function or one of its embodiments when the program portions are executed by the training system.

The invention relates, in a possible tenth embodiment, to a computer-readable storage medium on which are stored program portions that are readable and executable by a provision system, in order to carry out all the steps of the method for providing a difference image data record or its embodiments when the program portions are executed by the provision system.

The invention relates, in a possible eleventh embodiment, to a computer-readable storage medium on which are stored program portions that are readable and executable by a training system, in order to carry out all the steps of the method for providing a trained function or one of its embodiments when the program portions are executed by the training system.

The invention relates, in a twelfth embodiment, to a computer program or a computer-readable storage medium comprising a trained function provided through a method for providing a trained function or one of its embodiments.

A realization largely through software has the advantage that conventionally used provision units and/or training systems can also easily be upgraded with a software update in order to operate in the manner according to the invention. Such a computer program product can comprise, where relevant, in addition to the computer program product, further components, such as, for example, documentation and/or additional components including hardware components, for example, hardware keys (dongles, etc.) for using the software.

FIG. 1 shows an examination volume VOL with two vessels VES.1, VES.2, and a three-dimensional difference image data record DD. Herein, the image region of the difference image data record DDS corresponds to the examination volume VOL. In the example embodiment shown, the examination volume VOL comprises a first vessel VES.1 and a second vessel VES.2, wherein the first vessel VES.1 divides into two branches within the examination volume VOL. It is also possible that the examination volume VOL comprises no vessel VES.1, VES.2, exactly one vessel VES.1, VES.2 or more than two vessels VES.1, VES.2. The examination volume VOL comprises, apart from the vessels VES.1, VES.2, further structures OS.1, OS.2 which are not mapped in the three-dimensional first difference image data record DDS, since they are to be included with the background and therefore are not mapped in the three-dimensional first difference image data record.

In the example embodiment shown, the examination volume VOL and the difference image data record DDS extend relative to a first direction x, a second direction y and a third direction z. The first direction x, the second direction y and the third direction z are herein orthogonal in pairs.

Figure 2:
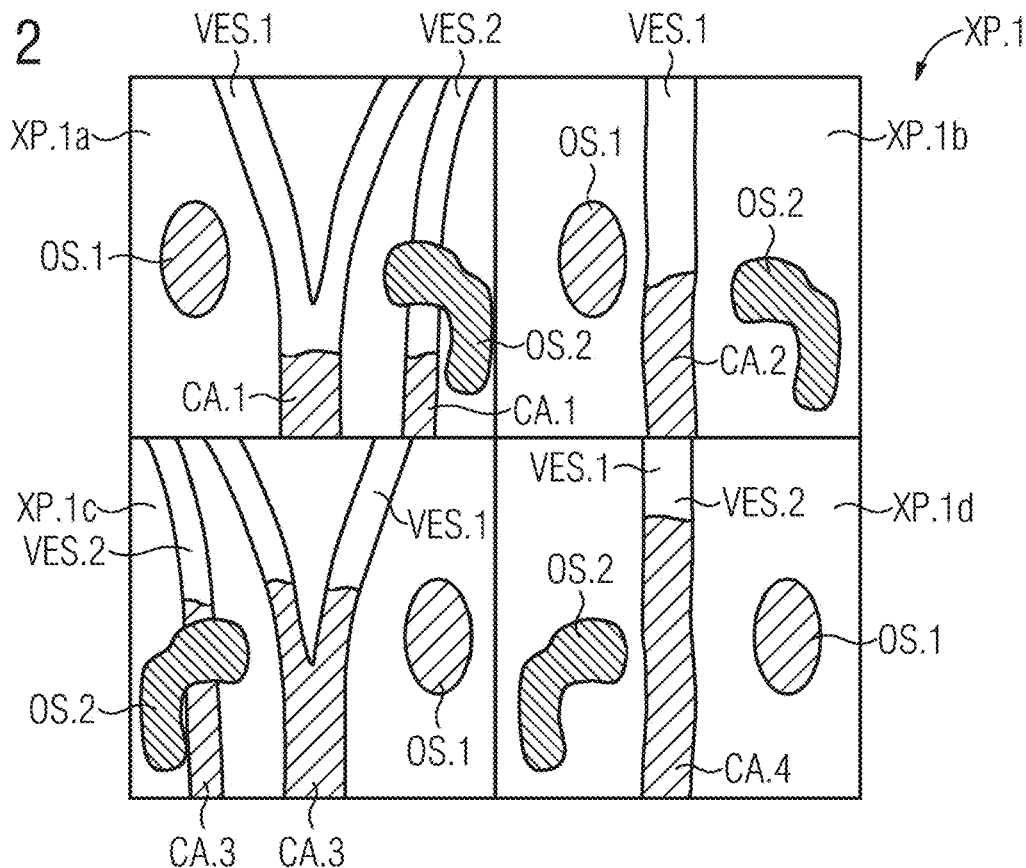
FIG. 2 shows two-dimensional first X-ray projections of the examination volume.
Figure 3:
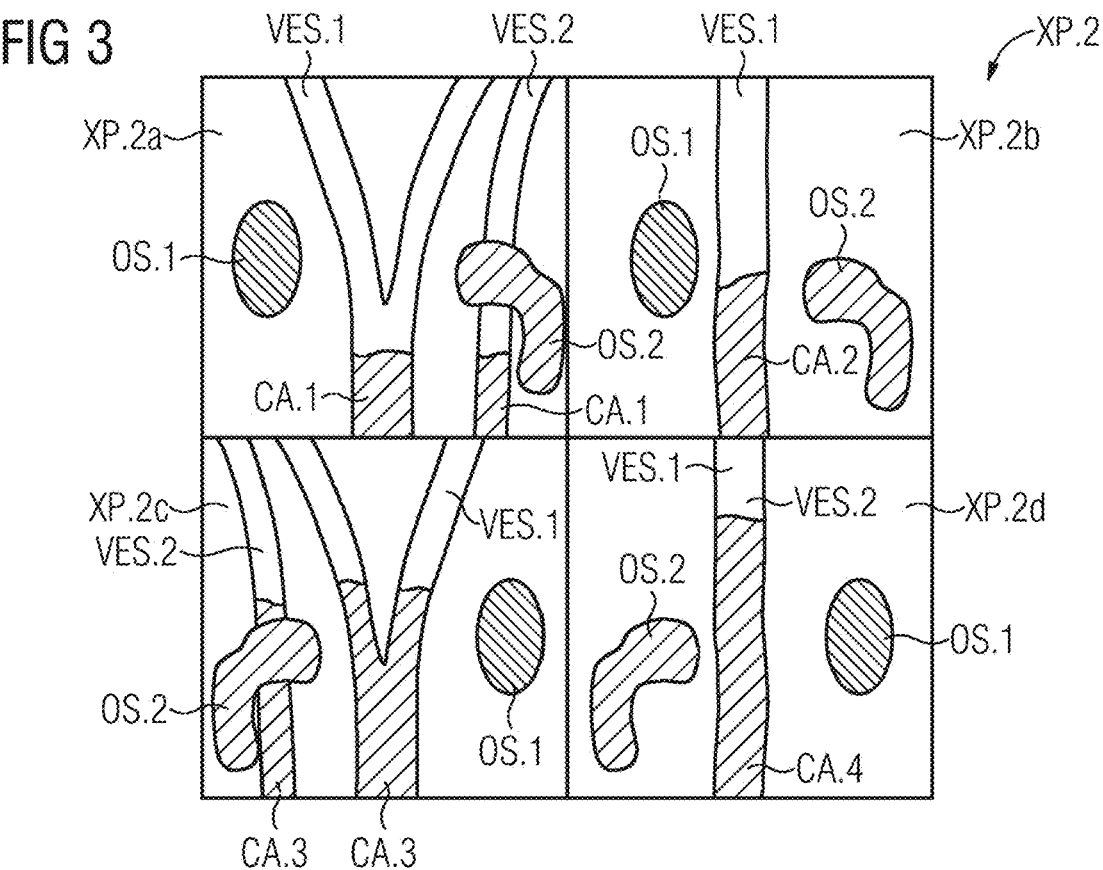
FIG. 3 shows two-dimensional second X-ray projections of the examination volume.

FIG. 2 shows a plurality of first X-ray projections XP.1a, ..., XP.1d of the examination volume VOL in respect of a first X-ray energy, while FIG. 3 shows a plurality of second X-ray projections XP.2a, ..., XP.2d of the examination volume VOL in respect of a second X-ray energy, wherein the second X-ray energy differs from the first X-ray energy. In the example embodiment shown, the first X-ray projections XP.1a, ..., XP.1d form a first real image data record RD.1 and the second X-ray projections XP.2a, ..., XP.2d form a second real image data record RD.2. Alternatively, the first real image data record RD.1 can also be determined based upon a three-dimensional reconstruction of the first X-ray projections XP.1a, ..., XP.1d, and/or the second real image data record RD.2 can be determined based upon a three-dimensional reconstruction of the second X-ray projections XP.2a, ..., CP.2d.

In the example embodiment shown, four two-dimensional X-ray projections XP.1a, ..., XP.1d, XP.2a, ..., XP.2d are shown in each case and more or fewer two-dimensional X-ray projections XP.1a, ..., XP.1d, XP.2a, ..., XP.2d can also be present or used.

Each of the two-dimensional X-ray projections XP.1a, ..., XP.1d, XP.2a, ..., XP.2d is herein an X-ray projection of the examination volume VOL in respect of a projection direction. Each of the two-dimensional X-ray projections XP.1a, XP.2a, is an X-ray projection of the examination volume VOL in respect of a projection direction, wherein the projection direction is antiparallel to the first direction x. Each of the two-dimensional X-ray projections XP.1b, XP.2b, is an X-ray projection of the examination volume VOL in respect of a projection direction, wherein the projection direction is antiparallel to the second direction y. Each of the two-dimensional X-ray projections XP.1c, XP.2c, is an X-ray projection of the examination volume VOL in respect of a projection direction, wherein the projection direction is parallel to the first direction x. Each of the two-dimensional X-ray projections XP.1d, XP.2d, is an X-ray projection of the examination volume VOL in respect of a projection direction, wherein the projection direction is parallel to the second direction y.

Furthermore, a time point is assigned to each of the two-dimensional X-ray projections XP.1a, ..., XP.1d, XP.2a, ..., XP.2d, wherein this time point in this example embodiment corresponds to the time point of the recording of the respective X-ray projection.

In the example embodiment shown, each of the two-dimensional X-ray projections XP.1a, ..., XP.1d, XP.2a, ..., XP.2d maps the vessels VES.1, VES.2 contained within the examination volume VOL. Furthermore, other structures OS.1, OS.2 in the examination volume VOL are mapped by the two-dimensional X-ray projections XP.1a, ..., XP.1d, XP.2a, ..., XP.2d.

At the different time points of the recording of the two-dimensional X-ray projections XP.1a, ..., XP.1d, XP.2a, ..., XP.2d, the vessels VES.1, VES.2 contain changeable concentrations CA.1, ..., CA.4 of contrast medium over time. Herein, the vessels VES.1, VES.2 have a contrast medium concentration CA.1 at the recording of the X-ray projections XP.1a, XP.2a. Furthermore, the vessels VES.1, VES.2 have a contrast medium concentration CA.2 at the recording of the X-ray projections XP.1b, XP.2b. Furthermore, the vessels VES.1, VES.2 have a contrast medium concentration CA.3 at the recording of the X-ray projections XP.1c, XP.2c. Furthermore, the vessels VES.1, VES.2 have a contrast medium concentration CA.4 at the recording of the X-ray projections XP.1d, XP.2d. The contrast medium is an X-ray contrast medium so that the respective contrast medium concentration CA.1, ..., CA.4 of the contrast medium is determinable from the X-ray projections. The contrast medium concentration CA.1, ..., CA.4 changes over time due to a static or dynamic liquid flow in the vessels VES.1, VES.2. In the example embodiment shown, the fluid is blood.

In the recording of the first X-ray projections XP.1a, ..., XP.1d with the first X-ray energy as shown in FIG. 2, the contrast medium and the first other structure OS.1 (for example, a bone structure) have a similar X-ray absorption. Therefore, the contrast medium and the first other structure OS.1 are barely to be distinguished, based upon the first X-ray projections XP.1a, ..., XP.1d. However, the contrast medium and the second other structure OS.2 (for example, a metal structure) have a different X-ray absorption and are therefore easy to distinguish.

In the recording of the second X-ray projections XP.2a, ..., XP.2d with the second X-ray energy as shown in FIG. 3, the contrast medium and the second other structure OS.2 (for example, a metal structure) have a similar X-ray absorption. Therefore, the contrast medium and the second other structure OS.2 are barely to be distinguished, based upon the second X-ray projections XP.2a, ..., XP.2d. However, the contrast medium and the first other structure OS.1 (for example, a metal structure) have a different X-ray absorption and are therefore easy to distinguish.

An exact differentiation between the contrast medium and the other structures OS.1, OS.2 is therefore advantageously possible by way of a first real image data record RD.1 and a multi-energetic real image data record RD.M.

Figure 4:
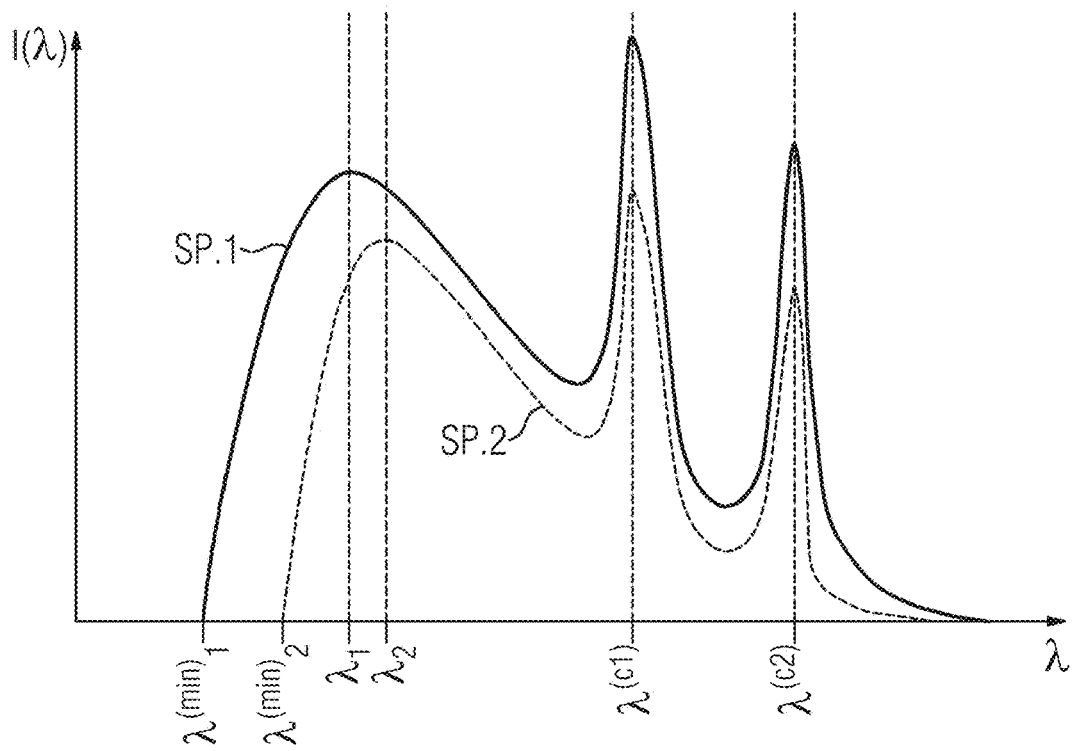
FIG. 4 shows a first X-ray spectrum and a second X-ray spectrum.

FIG. 4 shows a first X-ray spectrum SP.1 and a second X-ray spectrum SP.2 which have been generated via an X-ray tube as the X-ray source SRC.1, SRC.2. Herein, the first X-ray spectrum SP.1 corresponds to a first X-ray energy $E_1$ or a first accelerating voltage $U_1 = E_1/e$ (wherein e corresponds to the elementary charge), and the second X-ray spectrum corresponds to a second X-ray energy $E_2$ or a second accelerating voltage $U_2 = E_2/e$, wherein the first X-ray energy $E_1$ or the first accelerating voltage $U_1$ is greater than the second X-ray energy $E_2$ or the second accelerating voltage $U_2$. In the graph, the intensity $I(\lambda)$ of the X-ray radiation is given as a function of the wavelength $\lambda$ of the X-ray radiation. The intensity $I(\lambda)$ is herein proportional to the number of X-ray photons of the wavelength $\lambda$, which are generated by the X-ray source SRC.1, SRC.2.

According to the Duane-Hunt law, the X-ray spectrum SP.1, SP.2 has a minimum wavelength $\lambda^{(min)}$=hc/eU (wherein c is the velocity of light and h is the Planck constant), so that the minimum wavelength $\lambda^{(min)}_1$ of the first X-ray spectrum SP.1 is smaller here than the minimum wavelength $\lambda^{(min)}_2$ of the second X-ray spectrum. Furthermore, the X-ray spectrum according to Kramer's law has a relative intensity maximum at a wavelength of $\lambda_{1/2}$= $2\lambda^{(min)}_{1/2}$.

Furthermore, the first and second X-ray spectra SP.1, SP.2 have peaks of characteristic X-ray radiation at one or more characteristic wavelengths $\lambda^{(c1)}$, $\lambda^{(c2)}$. The characteristic wavelengths $\lambda^{(c1)}$, $\lambda^{(c2)}$ are herein not dependent upon the accelerating voltage $U_1$, $U_2$ or the X-ray energy $E_1$, $E_2$, but rather on the anode material of the X-ray tube. The characteristic X-ray radiation arises due to transitions between energy levels of the inner electron shell of the anode material.

Figure 5:
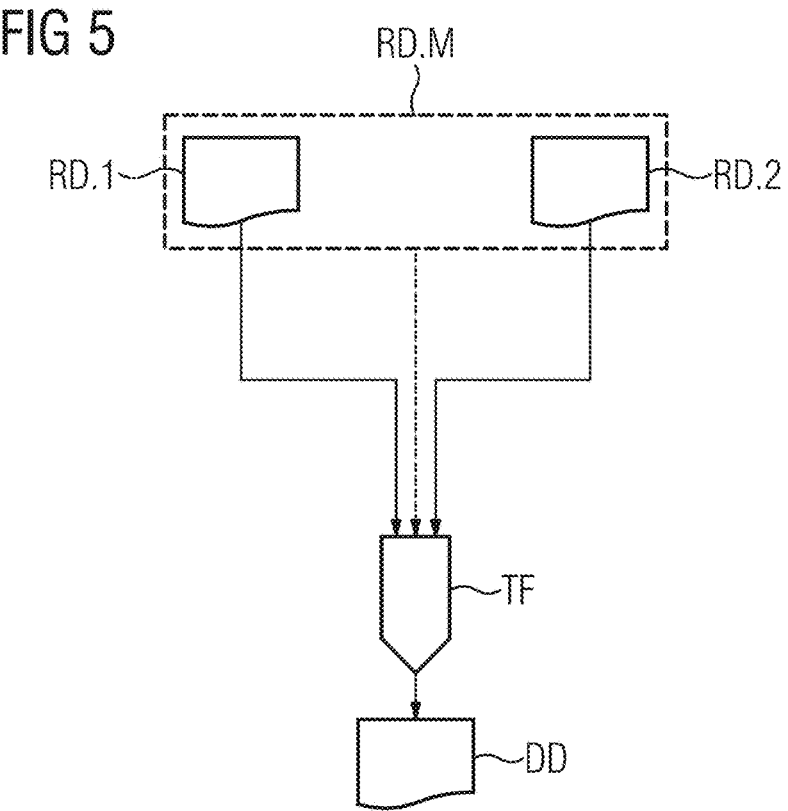
FIG. 5 shows a first example embodiment of the data flow of a method for determining a difference image data record.

FIG. 5 shows a first example embodiment of the data flow of a method for determining a difference image data record DD. In the example embodiment shown, the first real image data record RD.1 is a two-dimensional X-ray projection of an examination volume VOL in respect of the first X-ray energy E1, and the second real image data record RD.2 is a two-dimensional X-ray projection of the examination volume VOL in respect of the second X-ray energy E2. Advantageously, the first real image data record RD.1 and the second real image data record RD.2 have been recorded in relation to an identical projection direction. The multi-energetic real image data record RD.M comprises, in this example embodiment, the X-ray projection in respect of the first X-ray energy E1 and the X-ray projection in respect of the second X-ray energy E2. In particular therefore, in this example embodiment, the first real image data record RD.1, and the second real image data record RD.2 and also the multi-energetic real image data record RD.M are each two-dimensional image data records.

In this example embodiment, the trained function TF receives as input data the first real image data record RD.1 and the second real image data record RD.2. In this example embodiment, the input data of the trained function TF thus also comprises the multi-energetic real image data record RD.M.

Furthermore, in this example embodiment, the output data of the trained function TF corresponds to the difference image data record DD which, in this example embodiment, is also a two-dimensional image data record. Thus, in this example embodiment, the trained function TF is a function which maps two-dimensional image data records onto a further two-dimensional image data record.

In this example embodiment, the first real image data record RD.1 and the second real image data record RD.2 have the same extent measured in pixels in respect of both dimensions and also the difference image data record DD has in this example embodiment the same extent measured in pixels in respect of both dimensions as the first real image data record RD.1 and the second real image data record RD.2. For example, the first real image data record RD.1, the second real image data record RD.2 and the difference image data record have an extent of 512 pixels in respect of the first dimension and 512 pixels in respect of the second dimension.

Figure 6:
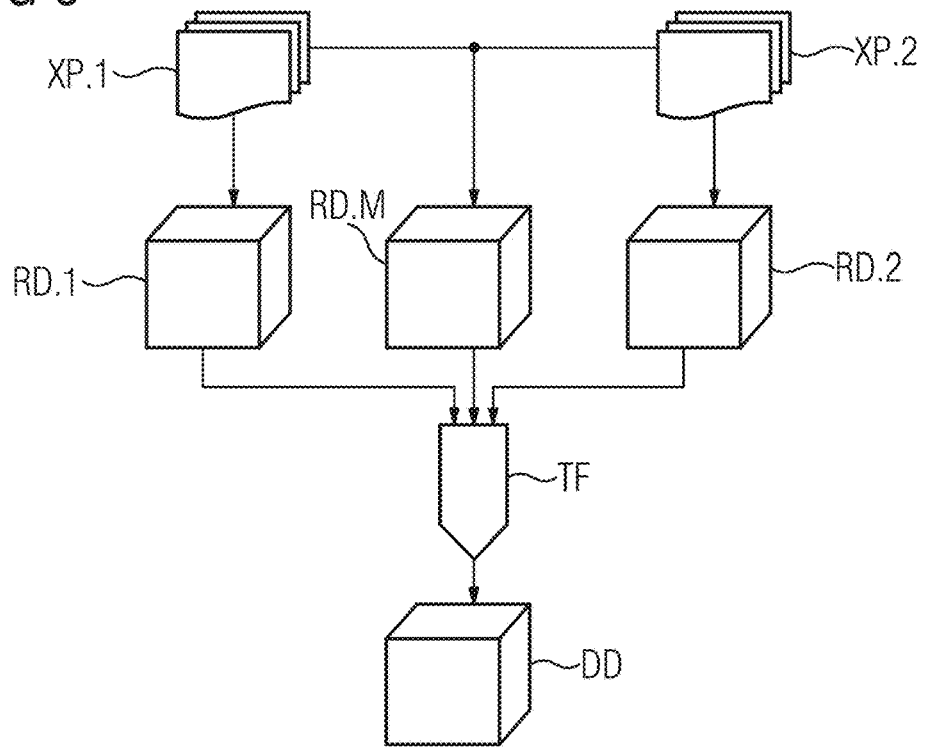
FIG. 6 shows a second example embodiment of the data flow of a method for determining a difference image data record.

FIG. 6 shows a second example embodiment of the data flow of a method for determining a difference image data record DD. In this example embodiment, the first real image data record RD.1, the second real image data record RD.2 and the multi-energetic real image data record RD.M are each three-dimensional image data records of an examination volume VOL, and the difference image data record DD is also a three-dimensional image data record of the examination volume VOL.

In this example embodiment, the first real image data record RD.1 is a three-dimensional reconstruction of first X-ray projections XP.1, wherein the first X-ray projections XP.1 are X-ray projections of the examination volume VOL in respect of the first X-ray energy E1. Furthermore, the second real image data record RD.2 is a three-dimensional reconstruction of second X-ray projections XP.2, wherein the second X-ray projections XP.2 are X-ray projections of the examination volume VOL in respect of the second X-ray energy E2. Furthermore, the multi-energetic real image data record RD.M is a three-dimensional reconstruction of the first X-ray projections XP.1 and the second X-ray projections XP.2. The first X-ray projections XP.1 and the second X-ray projections XP.2 are, in particular, two-dimensional X-ray projections of the examination volume VOL, in particular, in respect of a plurality of projection directions in each case.

In this example embodiment, the first real image data record RD.1 and the second real image data record RD.2 have the same extent measured in voxels in respect of each dimension. For example, the first real image data record RD.1 and the second real image data record RD.2 have an extent of 256 voxels in respect of the first dimension, in respect of the second dimension, an extent of 256 voxels, and in respect of the third dimension, an extent of 256 voxels (in total, therefore approximately $17 \cdot 10^6$ voxels). Furthermore, the multi-energetic real image data record RD.M has a greater extent measured in voxels, in respect of each dimension, in this example embodiment than the first real image data record RD.1. For example, the multi-energetic real image data record RD.M can have an extent of 512 voxels in respect of the first dimension, in respect of the second dimension, an extent of 512 voxels, and in respect of the third dimension, an extent of 512 voxels (in total, therefore approximately $134 \cdot 10^6$ voxels).

In this example embodiment, the trained function TF receives as input data the first real image data record RD.1, the second real image data record RD.2 and the multi-energetic real image data record RD.M. Alternatively, the trained function TF could receive as input data just the first real image data record RD.1 and the multi-energetic real image data record RD.M. Furthermore, as output data, the trained function TF generates the difference image data record DD, wherein the difference image data record DD is, in particular, a three-dimensional image data record DD. Thus the trained function TF is, in particular, a function which maps the three-dimensional image data records as input data onto a three-dimensional image data record as output data, wherein die three-dimensional image data records can, in particular, also have different extents.

Alternatively, the trained function TF can generate a probability data record as output data and the difference image data record DD can be determined by a voxel-wise multiplication of the probability data record with the multi-energetic real image data record RD.M.

In this example embodiment, the difference image data record DD has, in respect of each dimension, the same extent measured in voxels as the multi-energetic real image data record RD.M, in the alternative described, the probability data record is, in particular, a three-dimensional probability data record which, in respect of each dimension, has the same extent measured in voxels as the multi-energetic real image data record RD.M. For example, the difference image data record DD or the probability data record can have an extent of 512 voxels in respect of the first dimension, in respect of the second dimension, an extent of 512 voxels, and in respect of the third dimension, an extent of 512 voxels (in total, therefore approximately $134 \cdot 10^6$ voxels).

Figure 7:
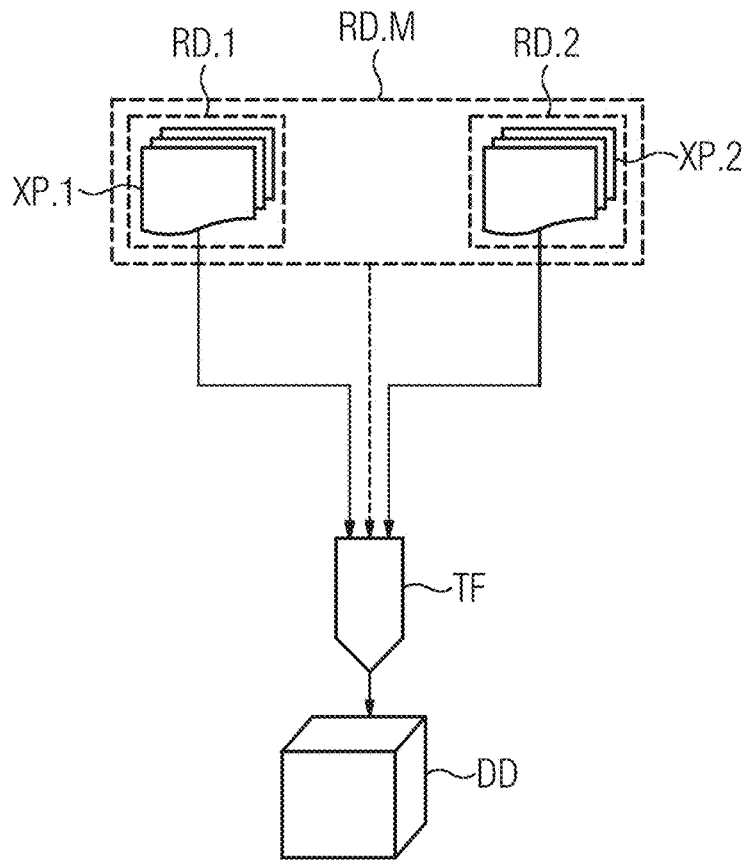
FIG. 7 shows a third example embodiment of the data flow of a method for determining a difference image data record.

FIG. 7 shows a third example embodiment of the data flow of a method for determining a difference image data record DD. In this example embodiment, the first real image data record RD.1 comprises a plurality of first X-ray projections XP.1, and the second real image data record RD.2 comprises a plurality of second X-ray projections XP.2. Furthermore, the multi-energetic real image data record RD.M comprises the plurality of first X-ray projections XP.1 and the plurality of second X-ray projections XP.2. In particular herein, the first X-ray projections XP.1 are X-ray projections of the examination volume VOL in respect of the first X-ray energy $E_1$ and the second X-ray projections XP.2 are X-ray projections of the examination volume VOL in respect of the second X-ray energy $E_2$.

In this example embodiment, the trained function TF receives as input data the first real image data record RD.1 and the second real image data record RD.2. Thus, the input data of the trained function TF is implicitly also based upon the multi-energetic real image data record RD.M. Furthermore, as output data, the trained function TF generates the difference image data record DD, wherein the difference image data record DD is, in particular, a three-dimensional image data record DD. Thus the trained function TF is, in particular, a function which maps a first plurality of two-dimensional X-ray projections and a second plurality of two-dimensional X-ray projections as input data onto a three-dimensional image data record as output data.

Figure 8:
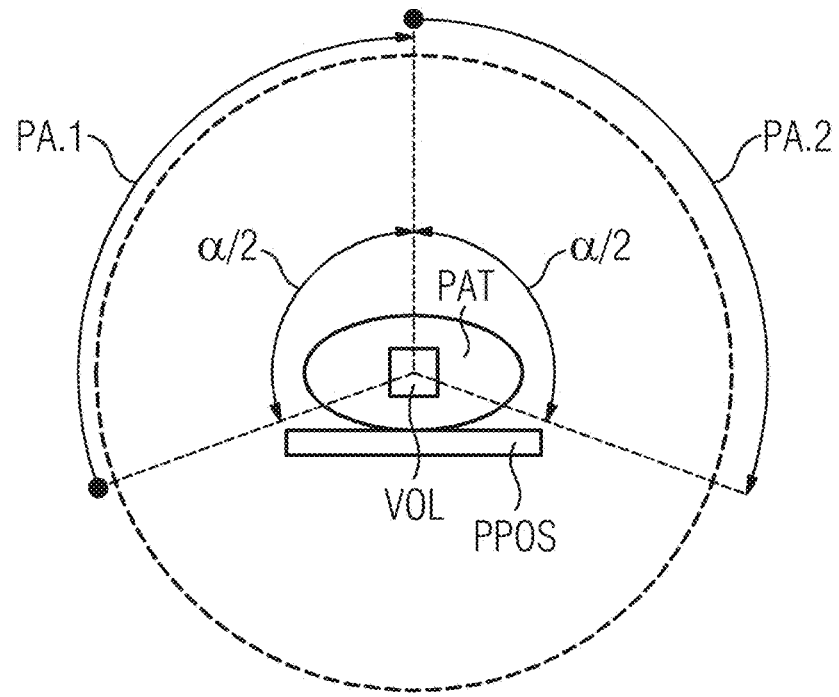
FIG. 8 shows a first example embodiment of a first projection angle region and a second projection angle region.

FIG. 8 shows a first example embodiment of a first projection angle region PA.1 and a second projection angle region PA.2. The projection angle regions PA.1, PA.2 shown can be used, in particular, for recording first X-ray projections XP.1 and/or second X-ray projections XP.2 upon which a first real image data record RD.1 and/or a second real image data record RD.2 and/or a multi-energetic real image data record RD.M are based.

The projection angle regions PA.1, PA.2 describe the projection directions of X-ray projections XP.1, XP.2 of an examination volume VOL. Herein, the examination volume VOL is part of a patient PAT, wherein the patient PAT is arranged on a patient positioning apparatus PPOS. Herein, the first projection angle region PA.1 shows possible positions, in particular, of a first X-ray source SRC.1 during the recording of first X-ray projections. Herein, the associated first X-ray detector DTC.1 is arranged on the opposite side of the first X-ray source SRC.1 relative to the examination volume VOL. Furthermore, the second projection angle region PA.2 shows possible positions of a first X-ray source SRC.1 or of a second X-ray source SRC.2 during the recording of second X-ray projections XP.2. Herein, the associated first X-ray detector DTC.1 or the associated second X-ray detector DTC.2 is arranged on the opposite side of the first X-ray source SRC.1 or the second X-ray source SRC.2 relative to the examination volume VOL. In particular, a projection angle region PA.1, PA.2 can also be interpreted as a set of projection directions.

In particular, the first projection angle region PA.1 can thus also be regarded as the locus curve of the first X-ray source SRC.1 on recording the first X-ray projections XP.1, and the second projection angle region PA.2 can also be regarded as the locus curve of the first X-ray source SRC.1 on recording the second X-ray projections XP.2, if the second X-ray projections XP.2 are recorded with the same X-ray source SRC.1 as the first X-ray projections XP.1, or as the locus curve of the second X-ray source SRC.2, if the second X-ray projections XP.2 are recorded with a second X-ray source SRC.2 that is distinct from the first X-ray source SRC.1.

In particular, the first projection angle region PA.1 can also be identified with a circular rotation of the first X-ray source SRC.1 around the examination volume VOL, wherein the first X-ray source SRC.1 describes a circular arc with an angle $\alpha/2$. Furthermore, in particular, the second projection angle region PA.2 can be identified with a circular rotation of the second X-ray source SRC.2 around the examination volume VOL, wherein the second X-ray source SRC.2 also describes a circular arc with an angle $\alpha/2$. Alternatively to the circular rotations and arcs, elliptical rotations or elliptical arcs or other at least partially concave movements of the first or the second X-ray source SRC.1, SRC.2 are possible. The angle $\alpha$ is herein, in particular, greater than 180°, in particular, the angle $\alpha$ corresponds to the sum of 180° and the aperture angle of the X-ray radiation emerging from the first or second X-ray source SRC.1, SRC.2. In particular, therefore, in this example embodiment, the angle $\alpha$ corresponds to 200°.

FIG. 8 shows the first projection angle region PA.1 and the second projection angle region PA.2 with a different radius. The different radii were selected, in particular, for reasons of the clarity of the drawing and do not imply, in particular, that the first X-ray source SRC.1 and the second X-ray source SRC.2 have different spacings from the examination volume VOL or from the center of rotation during the recording of the first X-ray projections XP.1 and the second X-ray projections XP.2.

Figure 9:
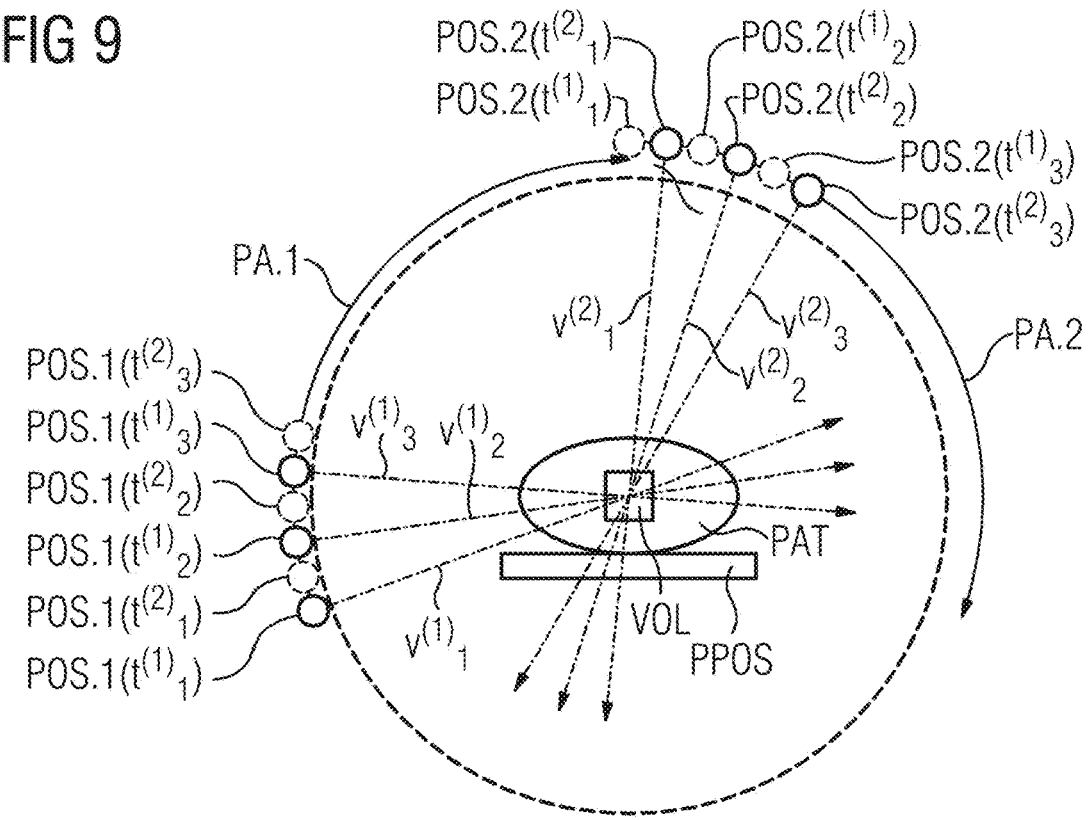
FIG. 9 shows possible positions of X-ray sources for the first example embodiment of a first projection angle region and a second projection angle region.

FIG. 9 shows possible positions $POS.1(t^{(1)}_1), \ldots, POS.2(t^{(2)}_3)$ of X-ray sources SRC.1, SRC.2 for the first example embodiment shown in FIG. 8 of a first projection angle region PA.1 and a second projection angle region PA.2.

Herein, POS.1($t$) denotes the position of a first X-ray source SRC.1 at the time point t, and POS.2($t$) denotes the position of a second X-ray source SRC.2 at the time point. Herein, the first X-ray source SRC.1 and the second X-ray source SRC.2 differ and the first X-ray source SRC.1 records first X-ray projections XP.1 in respect of a first X-ray energy $E_1$, and the second X-ray source SRC.2 records second X-ray projections XP.2 in respect of a second X-ray energy $E_2$.

In the example embodiment shown, the i-th X-ray projection of the first X-ray projections XP.1 is recorded at the time point $t^{(1)}_i$, wherein $t^{(1)}_i < t^{(1)}_j$ for i<j. Furthermore, in the example embodiment shown, the i-th X-ray projection of the second X-ray projections XP.2 is recorded at the time point $t^{(2)}_i$, wherein $t^{(2)}_i < t^{(2)}_j$ for i<j. Furthermore, in the example embodiment shown $t^{(1)}_i < t^{(2)}_i < t^{(1)}_{i+1}$ applies, alternatively however, other temporal sequences of the first and the second X-ray projections XP.1, XP.2 can be used. The time points $t^{(1)}_i$ can, in particular, be contained within the first X-ray projections XP.1, in particular as metadata, and furthermore, the time points $t^{(2)}_i$ can be contained, in particular, within the second X-ray projections XP.2.

At one of the positions $POS.1(t^{(1)}_i)$ (mapped in FIG. 9 are the positions $POS.1(t^{(1)}_1)$, $POS.1(t^{(1)}_2)$, $POS.1(t^{(1)}_3)$) of the first X-ray source SRC.1 at the time point $t^{(1)}_i$ (here $t^{(1)}_1$, $t^{(1)}_2$, $t^{(1)}_3$), the first X-ray source SRC.1 records one of the first X-ray projections XP.1 in respect of the first X-ray energy $E_1$ relative to a projection direction $v^{(1)}_i$ (here $v^{(1)}_1$, $v^{(1)}_2$, $v^{(1)}_3$). At the positions POS.1($t^{(2)}_i$) (mapped in FIG. 9 are the positions POS.1($t^{(2)}_1$), POS.1($t^{(2)}_2$), POS.1($t^{(2)}_3$)) of the first X-ray source SRC.1 at the time point $t^{(2)}_i$ (here $t^{(2)}_1$, $t^{(2)}_2$, $t^{(2)}_3$), the first X-ray source SRC.1 does not in general record any X-ray projection (except in the case $t^{(1)}_i = t^{(2)}_j$ for a pair i, j).

At one of the positions POS.2($t^{(2)}_i$) (mapped in FIG. 9 are the positions POS.2($t^{(2)}_1$), POS.2($t^{(2)}_2$), POS.2($t^{(2)}_3$)) of the second X-ray source SRC.2 at the time point $t^{(2)}_i$ (here $t^{(2)}_1$, $t^{(2)}_2$, $t^{(2)}_3$), the second X-ray source SRC.2 records one of the second X-ray projections XP.2 in respect of the second X-ray energy $E_2$ relative to a projection direction $v^{(2)}_i$ (here $v^{(2)}_1$, $v^{(2)}_2$, $v^{(2)}_3$). At the positions POS.2($t^{(1)}_i$) (mapped in FIG. 9 are the positions POS.2($t^{(1)}_1$), POS.2($t^{(1)}_2$), POS.2($t^{(1)}_3$)) of the second X-ray source SRC.2 at the time point $t^{(1)}_i$ (here $t^{(1)}_1$, $t^{(1)}_2$, $t^{(1)}_3$), the second X-ray source SRC.2 does not in general record any X-ray projection (except in the case $t^{(1)}_i = t^{(2)}_j$ for a pair i, j).

In FIG. 9, for reasons of clarity, in each case only the positions of the first X-ray source SRC.1 and the second X-ray source SRC.2 are shown for three X-ray projections XP.1, XP.2. In general, significantly more first X-ray projections XP.1, XP.2 are used and the positions of the first X-ray detector DTC.1 and of the second X-ray detector DTC.2 are situated along the projection direction $v^{(1)}_1$, $v^{(1)}_2$, $v^{(1)}_3$, $v^{(2)}_1$, $v^{(2)}_2$, $v^{(2)}_3$ on the side of the examination volume VOL opposite the first or second X-ray source SRC.1, SRC.2.

In FIG. 9, the first projection angle region PA.1 and the second projection angle region PA.2 are shown with different radii, and accordingly, the positions POS.1 ($t^{(1)}_1$), . . . , POS.2($t^{(2)}_3$)) have different spacings from the examination volume VOL. The different radii or the different spacings were selected, in particular, for reasons of the clarity of the drawing and do not imply, in particular, that the first X-ray source SRC.1 and the second X-ray source SRC.2 have different spacings from the examination volume VOL or from the center of rotation during the recording of the first X-ray projections XP.1 and the second X-ray projections XP.2.

Figure 10:
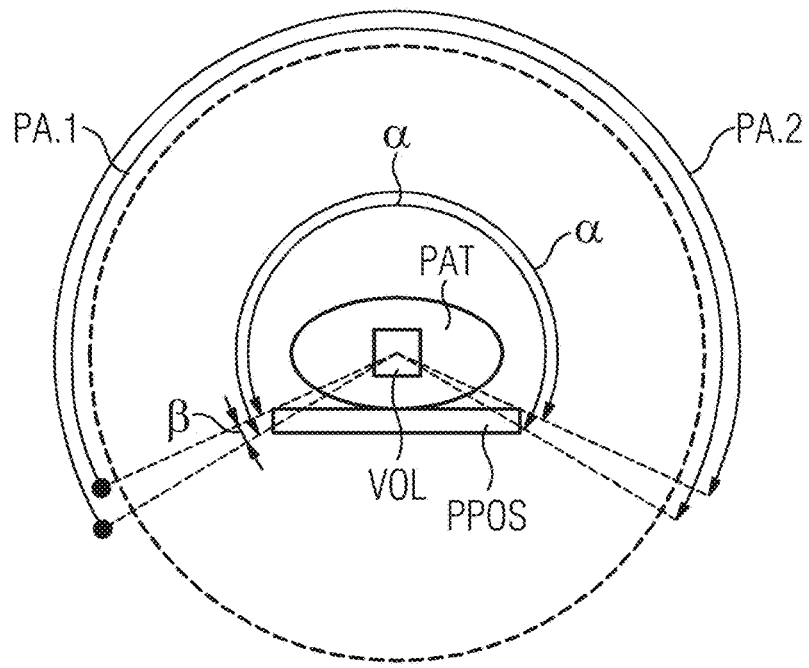
FIG. 10 shows a second example embodiment of a first projection angle region and a second projection angle region.

FIG. 10 shows a second example embodiment of a first projection angle region PA.1 and a second projection angle region PA.2. The projection angle regions PA.1, PA.2 shown can be used, in particular, for recording first X-ray projections XP.1 and/or second X-ray projections XP.2 upon which a first real image data record RD.1 and/or a second real image data record RD.2 and/or a multi-energetic real image data record RD.M are based. The significance of the projection angle regions PA.1, PA.2 for the positions of the first X-ray source SRC.1, of the first X-ray detector DTC.1, of the second X-ray source SRC.2 and of the second X-ray detector DTC.2 corresponds to the significance described in relation to FIG. 8.

In the second example embodiment shown, the first projection angle region PA.1 can also be identified with a circular rotation of the first X-ray source SRC.1 around the examination volume VOL, wherein the first X-ray source SRC.1 describes a circular arc with an angle α+β. Furthermore, in particular, the second projection angle region PA.2 can be identified with a circular rotation of the second X-ray source SRC.2 around the examination volume VOL, wherein the second X-ray source SRC.2 also describes a circular arc with an angle α+β. Alternatively to the circular rotations and arcs, elliptical rotations or elliptical arcs or other at least partially concave movements of the first or the second X-ray source SRC.1, SRC.2 are possible. The angle α is herein, in particular, greater than 180°, in particular, the angle α corresponds to the sum of 180° and the aperture angle of the X-ray radiation emerging from the first or second X-ray source SRC.1, SRC.2. In particular, therefore, in this example embodiment, the angle α corresponds to 200°. The angle β can correspond, in particular, to the minimum angle between the direction of the first X-ray source SRC.1 to the first X-ray detector DTC.1 and the direction of the second X-ray source SRC.2 to the second X-ray detector SRC.2. The angle β is thus restricted downwardly, in particular, by the extent and the geometrical form of the X-ray sources SRC.1, SRC.2 and the X-ray detectors DTC.1, DTC.2.

Figure 11:
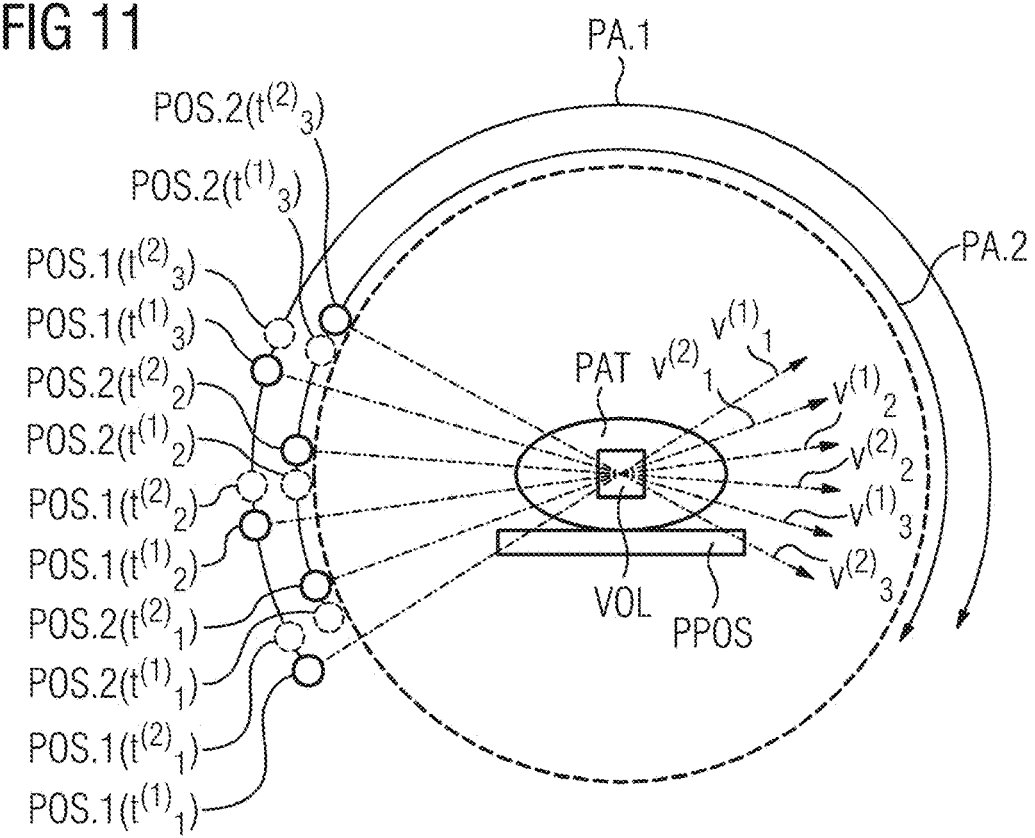
FIG. 11 shows possible positions of X-ray sources for the second example embodiment of a first projection angle region and a second projection angle region.

FIG. 11 shows possible positions POS.1($t^{(1)}_1$), . . . , POS.2($t^{(2)}_3$) of X-ray sources SRC.1, SRC.2 for the second example embodiment shown in FIG. 10 of a first projection angle region PA.1 and a second projection angle region PA.2. With regard to the objects represented, reference is made to the description in relation to FIG. 9.

In the second example embodiment shown, the first X-ray detector DTC.1 and the second X-ray detector DTC.2 have a constant, in particular, a minimum spacing, and/or the first X-ray source SRC.1 and the second X-ray source SRC.2 have a constant, in particular, a minimum spacing.

The projection angle regions PA.1, PA.2 shown in FIG. 10 and the positions shown in FIG. 11 can also serve as the basis for the recording with only one X-ray source SRC.1 and only one X-ray detector DTC.1, wherein the one X-ray source SRC.1 can be switched between the first X-ray energy and the second X-ray energy. Herein, the one first X-ray source records first X-ray projections XP.1 at the positions POS.1($t^{(1)}_1$), POS.1($t^{(1)}_2$), POS.1($t^{(1)}_3$) with the first X-ray energy and at the positions POS.2 ($t^{(2)}_1$), POS.2 ($t^{(2)}_2$), POS.2 ($t^{(2)}_3$), second X-ray projections XP.2 with the second X-ray energy. The remaining X-ray projections are irrelevant.

Figure 12:
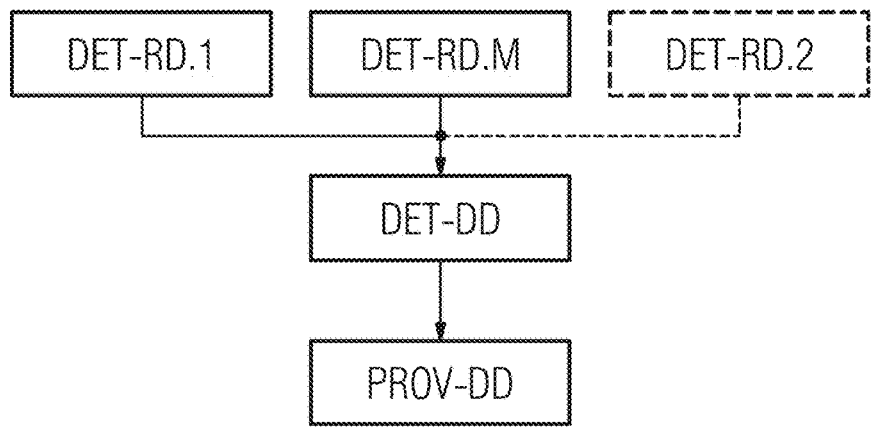
FIG. 12 shows a flow diagram of a first example embodiment of a method for providing a difference image data record.

FIG. 12 shows a flow diagram of a first example embodiment for providing a difference image data record DD.

The first step of the first example embodiment shown is the determination DET-RD.1 of a first real image data record RD.1 of an examination volume VOL in respect of a first X-ray energy $E_1$. Herein, the determination DET-RD.1 takes place through reception of the first real image data record RD.1 via an interface IF. A further step of the first example embodiment shown is the determination DET-RD.M of a multi-energetic real image data record RD.M of the examination volume VOL in respect of the first X-ray energy $E_1$ and a second X-ray energy $E_2$. Herein, the determination DET-RD.M takes place through reception of the second real image data record RD.2 via the interface IF.

Optionally, in the first example embodiment, a determination DET-RD.2 of a second real image data record RD.2 of the examination volume VOL in respect of the second X-ray energy E2 takes place. Herein, the determination DET-RD.2 takes place through reception of the second real image data record RD.2 via the interface IF.

As a further step in the example embodiment shown, the determination of the difference image data record DD of the examination volume VOL takes place through application of a trained function TF to input data, wherein the input data is based upon the first real image data record RD.1 and the multi-energetic real image data record RD.M. Optionally, the input data can also be based upon the second real image data record RD.2.

In a first variant of the first example embodiment, the first real image data record RD.1, the multi-energetic real image data record RD.M and the second real image data record RD.2 are each two-dimensional image data records, and the difference image data record DD is a two-dimensional difference image data record. Herein, the multi-energetic real image data record RD.M comprises the first and second real image data record RD.1, RD.2. This corresponds, for example, to the data flow shown in FIG. 5. The following applies $d=f_1(b^{(1)}, b^{(2)})$ (wherein d denotes the two-dimensional difference image data record DD, $b^{(1)}$ denotes the two-dimensional first real image data record RD.1, $b_{(2)}$ denotes the two-dimensional second real image data record RD.2, and wherein $f^1$ denotes the trained function TF). The input data of the trained function TF is herein implicitly based upon the multi-energetic real image data record RD.M in that it comprises the first and second real image data record RD.1, RD.2.

In a second variant of the first example embodiment, the first real image data record RD.1, the multi-energetic real image data record RD.M and the optional second real image data record RD.2 are each three-dimensional image data records, and the difference image data record DD is a three-dimensional difference image data record. This corresponds, for example, to the data flow shown in FIG. 6. The following applies $D=f_2(B^{(1)}, B^{(2)}, B^{(m)})$ and/or $D=f_2(B^{(2)}, B^{(m)})$ (wherein D denotes the three-dimensional difference image data record DD, $B^{(1)}$ denotes the three-dimensional first real image data record RD.1, $B^{(2)}$ denotes the three-dimensional second real image data record RD.2 and $B^{(m)}$ denotes the three-dimensional multi-energetic real image data record RD.M, and wherein $f^2$ denotes the trained function TF).

In a third variant of the first example embodiment, the first real image data record RD.1, the multi-energetic real image data record RD.M and the second real image data record RD.2 are each two-dimensional image data records, and the difference image data record DD is a three-dimensional difference image data record. Herein, the first real image data record RD.1 comprises a plurality of first X-ray projections XP.1 in respect of the first X-ray energy E1, and the second real image data record RD.2 comprises a plurality of second X-ray projections XP.2 in respect of the second X-ray energy E2. Furthermore, the multi-energetic real image data record RD.M comprises the first and the second X-ray projections XP.1, XP.2 and thus the first and the second real image data record RD.1, RD.2. This corresponds, for example, to the data flow shown in FIG. 7. The following applies $D=f_3(b^{(1)}_1, \ldots, b^{(1)}_m, b^{(2)}_1, \ldots, b^{(2)}_n)$ (wherein D denotes the three-dimensional difference image data record DD, $b^{(1)}_1, \ldots, b^{(1)}_m$ denotes the two-dimensional first real image data record RD.2 or the first X-ray projections XP.2 and $b^{(2)}_1, \ldots, b^{(2)}_n$ denotes the three-dimensional second real image data record RD.2 or the second X-ray projections XP.2, and wherein $f_3$ denotes the trained function TF). Herein, m is the number of the first X-ray projections XP.1 and n is the number of the second X-ray projections XP.2. In particular, n=m can apply, although n and m can also be different numbers. The input data of the trained function TF is herein implicitly based upon the multi-energetic real image data record RD.M in that it comprises the first and second real image data record RD.1, RD.2.

Herein, the trained function TF is a neural network, in particular, a convolutional neural network or a network comprising a convolution layer. The neural network can have, in particular, a "U-net" architecture, which is known, for example, from the publication by O. Ronneberger, P. Fischer, and T. Brox: "U-Net: Convolutional Networks for Biomedical Image Segmentation", MICCAI, 2015, the entire contents of which are hereby incorporated herein by reference.

The last step of the example embodiment shown is the provision PROV-DD of the difference image data record DD, herein via the interface IF. The provision PROV-DD of the difference image data record can comprise, in particular, the display, storage and/or transfer of the difference image data record DD.

Figure 13:
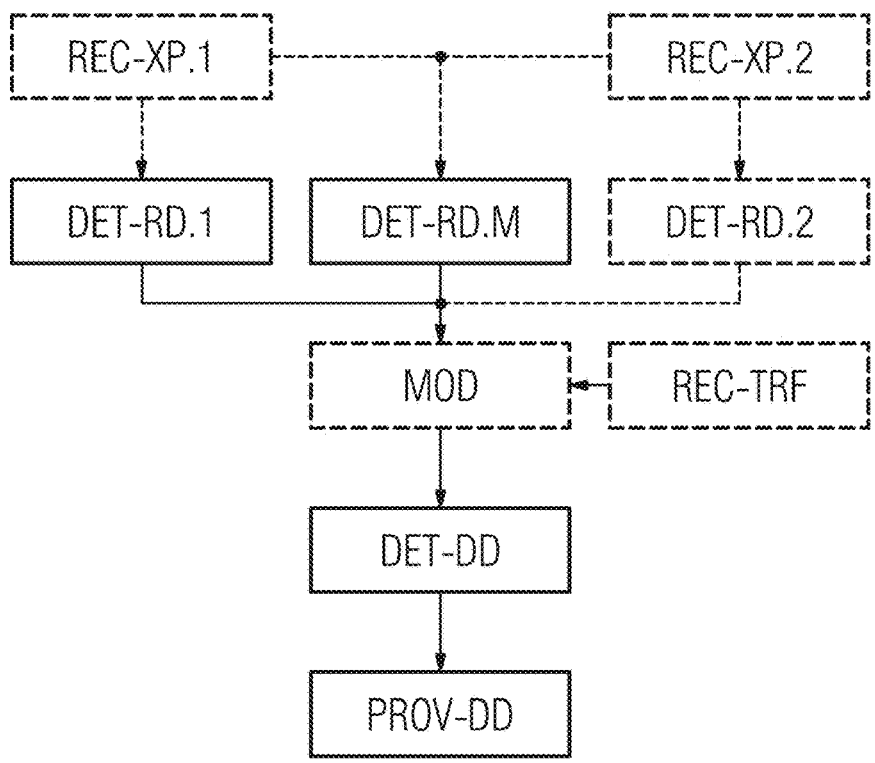
FIG. 13 shows a flow diagram of a second example embodiment of a method for providing a difference image data record.

FIG. 13 shows a flow diagram of a second example embodiment of the method for providing a difference image data record DD. The second example embodiment follows the data flow shown in FIG. 6.

The first steps of the second example embodiment are the reception REC-XP.1 of first X-ray projections XP.1 of the examination volume VOL in respect of a first X-ray energy $E_1$ via an interface IF and the reception REC-XP.2 of second X-ray projections XP.2 of the examination volume VOL in respect of a second X-ray energy $E_2$ via the interface IF, wherein the first X-ray energy $E_1$ differs from the second X-ray energy $E_2$.

Further steps of the second example embodiment are the determination DET-RD.1 of a first real image data record RD.1 of the examination volume VOL in respect of the first X-ray energy E1, and the determination DET-RD.2 of the second real image data record RD.2 of the examination volume VOL in respect of the second X-ray energy E2. Herein, the determination DET-RD.1 of the first real image data record RD.1 takes place by way of a three-dimensional reconstruction of the first X-ray projections XP.1 by a computer unit CU, and the determination DET-RD.2 of the second real image data record RD.2 by way of a three-dimensional reconstruction of the second X-ray projections XP.2 by the computer unit CU.

In the example embodiment shown, the three-dimensional reconstruction takes place by way of a filtered back-projection. Alternatively, iterative reconstructions or reconstructions based upon the Feldkamp algorithm are known.

In a mathematical notation, in this second example embodiment, the three-dimensional first real image data record RD.1 is given by $B^{(1)}=R(b^{(1)}_1, \ldots, b^{(1)}_m)$, and the second real image data record RD.2 by $B^{(2)}=R(b^{(2)}_1, \ldots, b^{(2)}_n)$. Herein, R denotes the reconstruction function, $b^{(1)}_i$ denotes the i-th (of the m overall) first X-ray projections XP.1, and $b^{(2)}_i$ denotes the i-th (of the n overall) second X-ray projections XP.2.

A further step of the second example embodiment is the determination DET-RD.M of a multi-energetic real image data record RD.M of the examination volume VOL in respect of the first X-ray energy $E_1$ and the second X-ray energy $E_2$ via the computer unit CU. Herein, the determination DET-RD.M of the multi-energetic real image data record RD.M takes place by way of a three-dimensional reconstruction of the first X-ray projections XP.1 and the second X-ray projections XP.2. In the example embodiment shown, the three-dimensional reconstruction takes place by way of a filtered back-projection. Alternatively, iterative reconstructions or reconstructions based upon the Feldkamp algorithm are known.

In a mathematical notation, in this second example embodiment, the three-dimensional multi-energetic real image data record RD.M is given by $B^{(m)}=R(b^{(1)}_1, \ldots, b^{(1)}_m, b^{(2)}_1, \ldots, b^{(2)}_n)$.

In the example embodiment shown, the trained function TF is applied to the three-dimensional first real image data record RD.1, to the three-dimensional second real image data record RD.2 and to the three-dimensional multi-energetic real image data record RD.M as input data and generates, as output data, a three-dimensional probability data record. In mathematical notation, this results in W=f($B^{(1)}$, $B^{(2)}$, $B^{(m)}$). This three-dimensional probability data record has, in respect of each of the three dimensions, the same extent measured in voxels as the three-dimensional multi-energetic real image data record RD.M, in particular, the three-dimensional probability data record thus assigns a probability value to each of the voxels of the three-dimensional multi-energetic real image data record RD.M. In particular, the probability value assigned to a voxel of the three-dimensional multi-energetic real image data record RD.M is a measure of the probability that this voxel maps contrast medium in the examination volume VOL or that this voxel maps a vessel VES.1, VES.2 in the examination volume VOL.

Further steps of the second example embodiment are the reception REC-TRF of a transfer function via the interface IF and the modification MOD of the at least three-dimensional probability data record based upon the transfer function via the computer unit CU. Herein, the transfer function T: $[0, 1] \rightarrow [0, 1]$ is a function which maps probability values onto probability values, and is in particular, a monotonically increasing function. The modification MOD takes place through voxel-wise application of the transfer function to the probability data record, and the following applies, $W'_{ijk}=T(W)_{ijk}=T(W_{ijk})$, where W' is the modified probability data record.

Furthermore, in this example embodiment, the determination DET-DD of the difference image data record DD takes place through voxel-wise multiplication of the modified probability data record by the multi-energetic real image data record RD.M, and it thus applies that $D=T(W)\cdot B^{(m)}=T(f(B^{(1)}, B^{(2)}, B^{(m)}))\cdot B^{(m)}$. Alternatively, the modification MOD of the probability data record can also be dispensed with and, in this case, the difference image data record can be determined by multiplication of the probability data record by the multi-energetic real image data record RD.M, that is through $D=W\cdot B^{(m)}=f(B^{(1)}, B^{(2)}, B^{(m)})\cdot B^{(m)}$.

Figure 14:
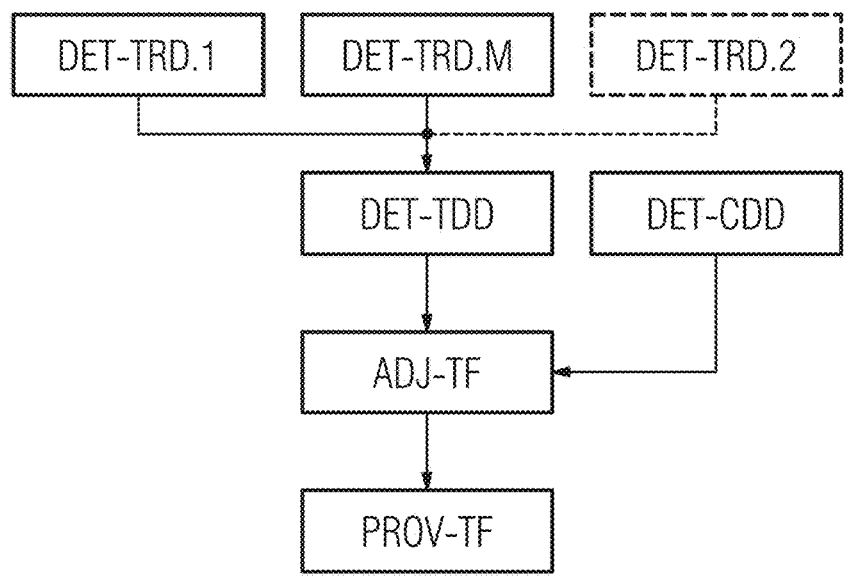
FIG. 14 shows a flow diagram of a first example embodiment of a method for providing a trained function.

FIG. 14 shows a flow diagram of a first example embodiment of a method for providing a trained function. The first steps of the first example embodiment are the determination of a first training real image data record of a training examination volume in respect of a first X-ray energy and the determination of a multi-energetic training real image data record of the training examination volume in respect of the first training X-ray energy and a second training X-ray energy, wherein the second training X-ray energy differs from the first training X-ray energy. Furthermore, the first example embodiment comprises the optional step of determining a second training real image data record of the training examination volume in respect of the second training X-ray energy. In the first example embodiment, both the first training real image data record and also the second training real image data record and the multi-energetic training real image data record are received via a training interface TIF.

Alternatively, via the training interface, first training X-ray projections of the training examination volume in respect of the first training X-ray energy can also be received, and the first training real image data record can be determined as a three-dimensional reconstruction of the first training X-ray projections via the training computer unit. Furthermore, via the training interface, second training X-ray projections of the training examination volume in respect of the second training X-ray energy can also be received, and the second training real image data record can be determined as a three-dimensional reconstruction of the second training X-ray projections via the training computer unit.

A further step of the first example embodiment is the determination DET-CDD of a comparison difference image data record of the training examination volume. The comparison difference image data record is herein, in particular, a difference image data record of the training examination volume and constitutes the ground truth of the training method. In the first example embodiment, the comparison difference image data record is received via the training interface.

A further step of the first example embodiment is the determination DET-TDD of a training difference image data record of the training examination volume by application of the trained function to input data, wherein the input data is based upon the first training real image data record and upon the multi-energetic training real image data record. Optionally, the input data is further based on the second training real image data record.

Herein, the trained function TF is a neural network, in particular, a convolutional neural network or a network comprising a convolution layer. The neural network can have, in particular, a "U-net" architecture, which is known, for example, from the publication by O. Ronneberger, P. Fischer, and T. Brox: "U-Net: Convolutional Networks for Biomedical Image Segmentation", MICCAI, 2015, the entire contents of which are hereby incorporated herein by reference.

Herein the training difference image data record and the comparison difference image data record have the same dimension and the extent of the training difference image data record measured in pixels or voxels in relation to each dimension is identical to the extent of the comparison difference image data record measured in pixels or voxels.

A further step of the example embodiment shown is the adaptation ADJ-TF of the trained function based upon a comparison of the training difference image data record and the comparison difference image data record. In particular, the adaptation takes place based upon a cost function which evaluates the deviation between the training difference image data record and the comparison difference image data record. In particular, the cost function can be the total of the squares of the deviations of the individual pixels or voxels of the training difference image data record and of the comparison difference image data record. In this example embodiment, the trained function is an artificial neural network and the adaptation of the artificial neural network comprises the adaptation of at least one edge weight of the artificial neural network, and the adaptation is based upon the backpropagation algorithm.

The last step of the first example embodiment shown is the provision PROV-TF of the trained function. In the example embodiment shown, the trained function is stored but alternatively, the trained function (or one or more of its parameters) can also be displayed, or transferred for further processing.

In the first example embodiment, the first and the second training real image data record and the training and comparison difference image data records can be two-dimensional image data records. Herein, the data structures are similar to FIG. 5. In this case, the multi-energetic training real image data record comprises the first and second training real image data record.

Alternatively, the first, the second and the multi-energetic training real image data record and the training and comparison difference image data records can be three-dimensional image data records. Herein, the data structures are similar to FIG. 6.

Alternatively, the first and the second training real image data records can each comprise a plurality of two-dimensional X-ray projections and the training and comparison difference image data records are three-dimensional image data records. Herein, the data structures are similar to FIG. 6, and in particular, the multi-energetic training real image data record comprises the first and the second training real image data record.

Figure 15:
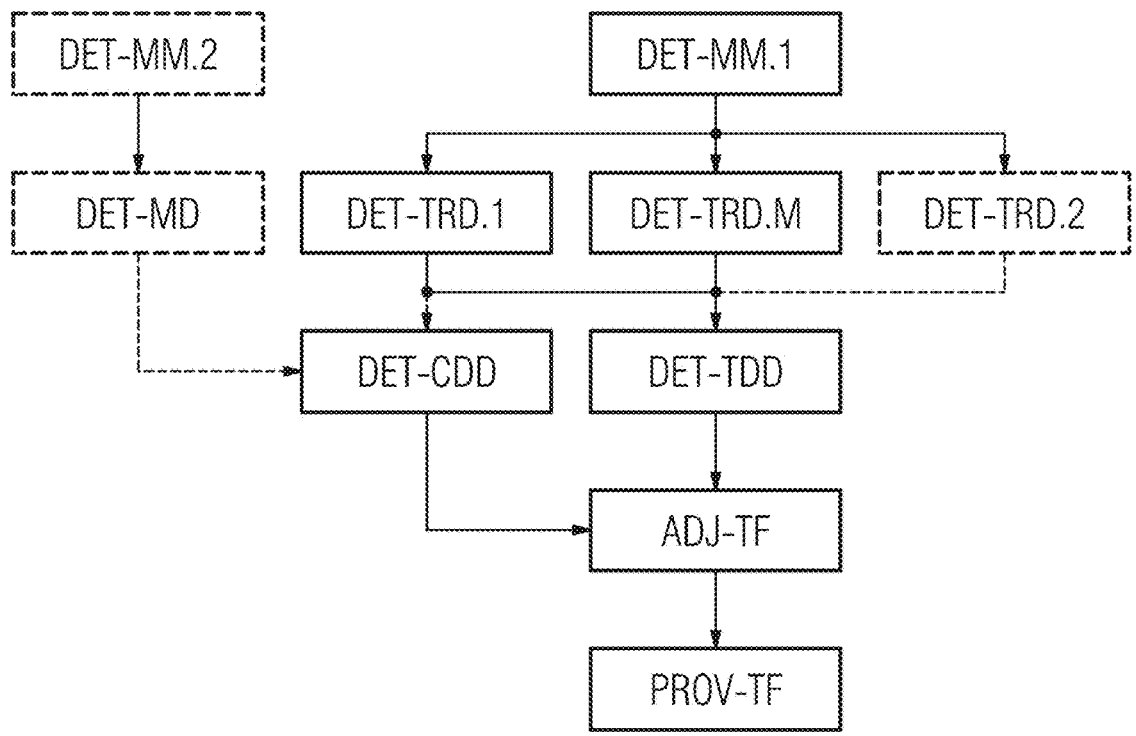
FIG. 15 shows a flow diagram of a second example embodiment of a method for providing a trained function.

FIG. 15 shows a flow diagram of a second example embodiment of the method for providing a trained function. The second example embodiment has all the steps of the first example embodiment shown in FIG. 14, and can, in particular, also have the advantageous configurations and developments described there.

The example embodiment shown further comprises the reception DET-MM.1 of a first three-dimensional material model of the training examination volume and the reception DET-MM.2 of a second three-dimensional material model of the training examination volume, in particular, in each case, with the training interface TIF. Herein, the first three-dimensional material model is a material model of the training examination volume including contrast medium, and the second three-dimensional material model is a material model of the training examination volume without contrast medium.

A material model describes, in this second example embodiment, a three-dimensional spatial distribution of an energy-dependent X-ray absorption coefficient $\mu(x, E)$. In this example embodiment, the material model is continuous, i.e. a function of the three-dimensional spatial coordinates x, in particular a constant function or in particular, a differentiable function of the spatial coordinate x. In particular, with a regular arrangement of the voxels, the material model can be described by way of an indexed energy-dependent X-ray absorption coefficient $\mu_{ijk}(E)$. The material model can further be defined for an arbitrary number of X-ray energies E, but it is sufficient to give the material model only for the first and second training X-ray energy, that is $\mu^{(1)}(x)$ and/or $\mu^{(1)}_{ijk}$ for the first training X-ray energy and $\mu^{(2)}(x)$ and/or $\mu^{(2)}_{ijk}$ for the second training X-ray energy.

In the second example embodiment shown, the first training real image data record TRD.1 and the second training real image data record TRD.2 are each three-dimensional image data records of the training examination volume, comprising 256·256·256 voxels, and the multi-energetic training real image data record TRD.M is a three-dimensional training real image data record of the examination volume comprising 512·512·512 voxels, and the first material model also comprises 512·512·512 voxels. The first training real image data record TRD.1 and the second training real image data record TRD.2 are then calculated as $B_{ijk}^{(1/2)} = \sum_{i'=2i}^{2i+1} \sum_{j'=2j}^{2j+1} \sum_{k'=2k}^{2k+1} \mu_{i'j'k'}^{(1/2)}$, and the multi-energetic training real image data record TRD.M is calculated as $B_{ijk}^{(m)} = (\mu_{ijk}^{(1)} + \mu_{ijk}^{(2)})/2$.

Alternatively, two-dimensional first training X-ray projections and two-dimensional second training X-ray projections based upon the first material model can also be determined, wherein the first training X-ray projections are X-ray projections of the training examination volume in respect of the first training X-ray energy, and wherein the second training X-ray projections are X-ray projections of the training examination volume in respect of the second training X-ray energy. In particular, the three-dimensional first training real image data record can then be reconstructed based upon the first training X-ray projections, the three-dimensional second training real image data record can be reconstructed based upon the second training X-ray projections, and the multi-energetic training real image data record can be reconstructed based upon the first training X-ray projections and the second training X-ray projections. The training X-ray projections are given in this case by the equation $$b^{(1/2)}(y,v) \propto \int_{\Gamma(y,v)} \mu^{(1/2)}(x) dx$$

wherein $\Gamma(y, v)$ is the path from the X-ray source to the X-ray detector at the coordinate y if the projection direction corresponds to the angle v. In particular, in this case, the first material model can also be formed as changeable over time in order to simulate a changeable density of contrast medium in the training examination volume over time.

The second example embodiment shown further comprises the determination DET-MD of a mask image data record of the training examination volume. In this case, the mask image data record is determined based upon the second three-dimensional material model, for example as $M_{ijk} = (v_{ijk}^{(1)} + v_{ijk}^{(2)})/2$ (herein v denotes the second material model). Alternatively, the mask image data record can also be received directly via the training interface.

In particular, the mask image data record can also be determined from a three-dimensional reconstruction of two-dimensional X-ray projections, wherein these can be determined from $$m^{(1/2)}(y,v) \propto \int_{\Gamma(y,v)} v^{(1/2)}(x) dx.$$

The mask image data record can herein be determined based only upon the X-ray projections $m^{(1)}$ in respect of the first training X-ray energy, based only upon the X-ray projections $m^{(2)}$ in respect of the second training X-ray energy, or based upon both the X-ray projections $m^{(1)}$ in respect of the first training X-ray energy as well as upon the X-ray projections $m^{(2)}$ in respect of the second training X-ray energy.

In the example embodiment shown, the determination DET-CDD of the comparison difference image data record then takes place by way of a digital subtraction angiography based upon the mask image data record and the multi-energetic training real image data record, that is with $B^{(m)}_{ijk} - M_{ijk}$. Alternatively, the comparison difference image data record can also be determined by way of a digital subtraction angiography based upon the mask image data record and the first training real image data record or by way of a digital subtraction angiography based upon the mask image data record and the second training real image data record.

Figure 16:
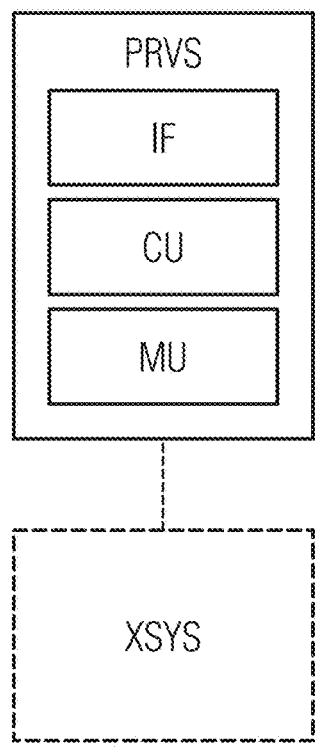
FIG. 16 shows an example embodiment of a provision system.
Figure 17:
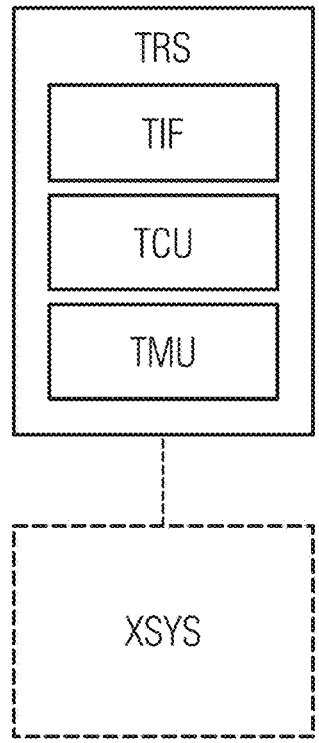
FIG. 17 shows an example embodiment of a training system.

FIG. 16 shows a provision system PRVS and FIG. 17 shows a training system TRS. The provision system PRVS shown is configured to carry out an inventive method for providing a difference image data record DD. The training system shown is configured to carry out an inventive method for providing a trained function TF. The provision system PRVS comprises an interface IF, a computer unit CU and a storage unit MU; the training system TRS comprises a training interface TIF, a training computer unit TCU and a training storage unit TMU.

The provision system PRVS and/or the training system TRS can be, in particular, a computer, a microcontroller or an integrated circuit. Alternatively, the provision system PRVS and/or the training system TRS can be a real or virtual grouping of computers (a technical term therefor being "cluster" or, in the case of a virtual grouping, "cloud"). The provision system PRVS and/or the training system TRS can also be configured as a virtual system which is executed on a real computer or a real or virtual grouping of computers (a technical term therefor being "virtualization").

An interface IF and/or a training interface TIF can be a hardware or software interface (for example, PCI bus, USB or Firewire). A computer unit CU and/or a training computer unit TCU can comprise hardware elements or software elements, for example, a microprocessor or a so-called FPGA (Field Programmable Gate Array). A storage unit MU and/or a training storage unit MTU can be realized as a non-permanent working memory (Random Access Memory, RAM) or as a permanent mass storage unit (hard disk, USB stick, SD card, solid state disk).

The interface IF and/or the training interface TIF can comprise, in particular, a plurality of subsidiary interfaces which carry out the different steps of the respective method. In other words, the interface IF and/or the training interface TIF can also be regarded as a plurality of interfaces IF or a plurality of training interfaces TIF. The computer unit CU and/or the training computer unit TCU can comprise, in particular, a plurality of subsidiary computer units which carry out the different steps of the respective method. In other words, the computer unit CU and/or the training computer unit TCU can also be regarded as a plurality of computer units CU or a plurality of training computer units TCU.

Figure 18:
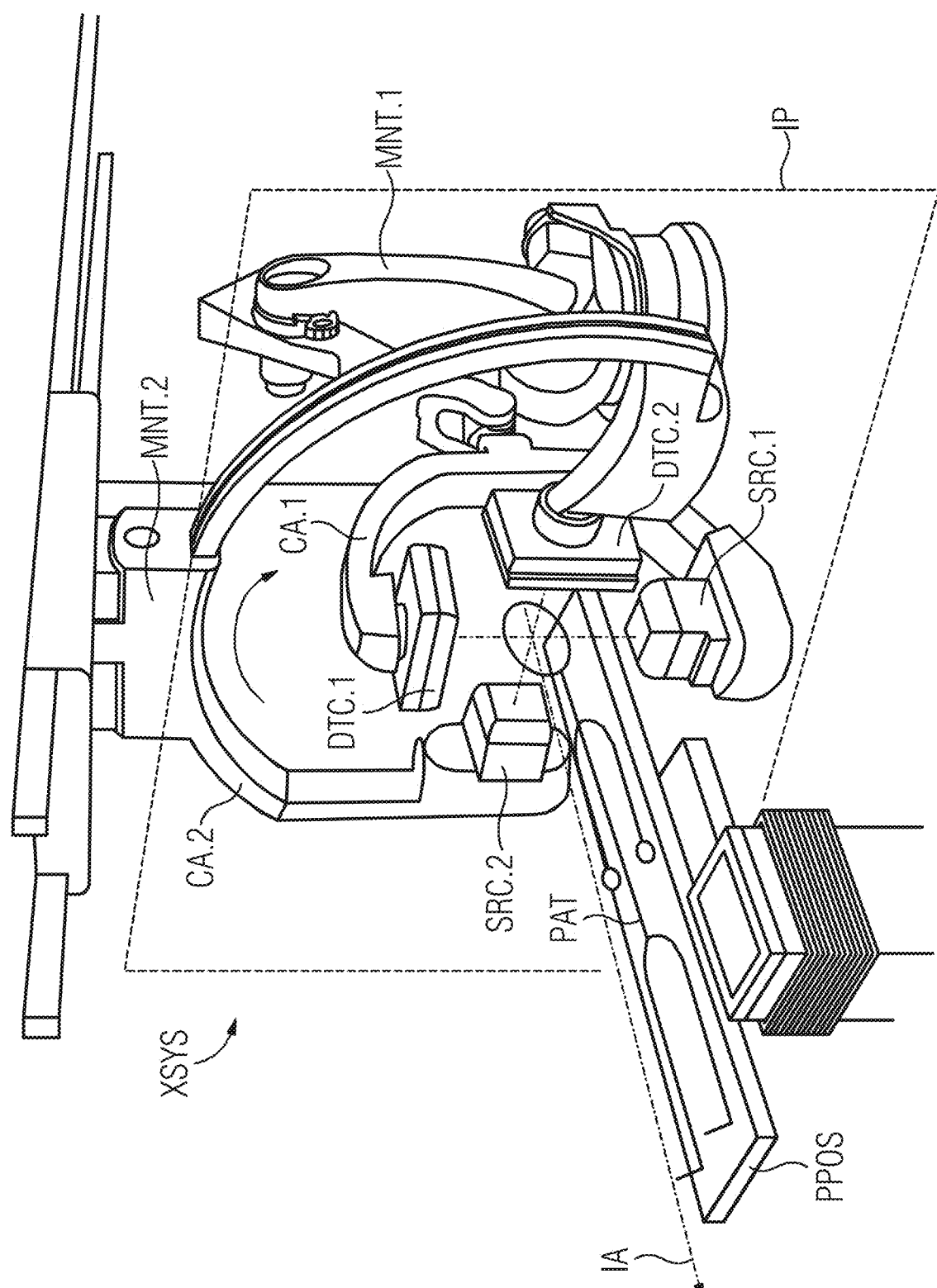
FIG. 18 shows an X-ray device.

FIG. 18 shows an example embodiment of an X-ray device XSYS. The X-ray device XSYS is herein configured as a double C-arm X-ray device. The X-ray device comprises a first C-arm CA.1 and arranged at the first end of the first C-arm CA.1 is a first X-ray source SRC.1, and at the second end of the first C-arm CA.1 is a first X-ray detector DTC.2. The X-ray device further comprises a second C-arm CA.2 and arranged at the first end of the first C-arm CA.2 is a second X-ray source SRC.2, and arranged at the second end of the second C-arm CA.2 is a second X-ray detector. The first C-arm CA.1 is arranged on a first mounting MNT.1, wherein the first mounting is configured as a multi-axis articulated robot. The second C-arm CA.2 is arranged on a second mounting MNT.2, wherein the second mounting comprises a ceiling fixing.

The first X-ray source SRC.1 and the second X-ray source SRC.2 are, in particular, an X-ray tube which have, in particular, the same anode material. The first X-ray detector DTC.1 and the second X-ray detector are, in particular, flat panel detectors.

The X-ray sources SRC.1, SRC.2 and the X-ray detectors DTC.1, DTC.2 are herein configured for rotation about an imaging axis IA, in particular for circular rotation about the imaging axis IA. The imaging axis IA herein intersects, in particular, the examination volume VOL. On rotation about the imaging axis, the X-ray sources SRC.1, SRC.2 and the X-ray detectors move in an imaging plane IP, wherein the imaging plane IP is arranged orthogonal to the imaging axis IA. The X-ray sources SRC.1, SRC.2 and the X-ray detectors DTC.1, DTC.2 are herein configured to rotate about the imaging axis IA, in that the C-arm CA.1, CA.2 is configured to rotate about the imaging axis IA.

The X-ray device XSYS further comprises a patient positioning apparatus PPOS, wherein the patient positioning apparatus PPOS is configured for positioning a patient PAT. In particular, the patient PAT can be displaced via the patient positioning apparatus along the imaging axis IA.

Where it has not yet explicitly been set out, although useful and in the spirit of the invention, individual example embodiments, individual sub-aspects or features thereof can be combined or exchanged with one another without departing from the scope of the present invention. Advantages of the invention described in relation to an example embodiment also apply without explicit mention, where transferable, to other example embodiments.

The patent claims of the application are formulation proposals without prejudice for obtaining more extensive patent protection. The applicant reserves the right to claim even further combinations of features previously disclosed only in the description and/or drawings.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

None of the elements recited in the claims are intended to be a means-plus-function element within the meaning of 35 U.S.C. § 112(f) unless an element is expressly recited using the phrase "means for" or, in the case of a method claim, using the phrases "operation for" or "step for."

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A computer-implemented method for providing a difference image data record of an examination volume, comprising:
    determining a first real image data record of the examination volume in respect of a first X-ray energy;
    determining a multi-energetic real image data record of the examination volume in respect of the first X-ray energy and a second X-ray energy, the second X-ray energy differing from the first X-ray energy; and
    determining the difference image data record of the examination volume by application of a trained function to input data, the input data being based upon the first real image data record determined and the multi-energetic real image data record determined; and
    providing the difference image data record.

2. The method of claim 1, further comprising:
    determining a second real image data record of an examination volume in respect of a second X-ray energy; and
wherein the input data is further based upon the second real image data record.

3. The method of claim 1, further comprising:
    receiving first X-ray projections of the examination volume in respect of the first X-ray energy; and
    receiving second X-ray projections of the examination volume in respect of the second X-ray energy, wherein the first real image data record is at least one of based upon the first X-ray projections and includes the first X-ray projections.

4. The method of claim 3, wherein the first real image data record is based upon an at least three-dimensional reconstruction of the first X-ray projections.

5. The method of claim 3, wherein at least one of
during recording of the first X-ray projections, the examination volume includes contrast medium, and
during recording of the second X-ray projections, the examination volume includes contrast medium.

6. The method of claim 3, wherein the first X-ray projections and the second X-ray projections have been recorded simultaneously.

7. The method of claim 3, wherein the first X-ray projections are recordings of a first X-ray source and of a first X-ray detector, and wherein the second X-ray projections are recordings of a second X-ray source and of a second X-ray detector.

8. The method of claim 7, wherein a biplanar X-ray device includes the first X-ray source, the second X-ray source, the first X-ray detector and the second X-ray detector.

9. The method of claim 3, wherein each of the first X-ray projections is an X-ray projection of the examination volume in respect of a projection direction from a first projection angle region, wherein each of the second X-ray projections is an X-ray projection of the examination volume in respect of a projection direction from a second projection angle region,
and wherein the first projection angle region and the second projection angle region differ.

10. The method of claim 9, wherein the first projection angle region and the second projection angle region are disjoint.

11. The method of claim 10, wherein at least one of
an overlap of the first projection angle region and the second projection angle region comprises at least 50% of at least one of the first projection angle region and of the second projection angle region.

12. The method of claim 4, wherein output data of the trained function includes a probability data record, wherein the difference image data record is based upon the probability data record.

13. The method of claim 12, further comprising:
receiving another transfer function,
modifying an at least three-dimensional probability data record based upon the another transfer function received.

14. The method of claim 12, wherein the difference image data record is based upon a multiplication of the probability data record by the first real image data record.

15. A computer-implemented method for providing a trained function, comprising:
determining a first training real image data record of a training examination volume in respect of a first training X-ray energy;
determining a multi-energetic training real image data record of the training examination volume in respect of the first training X-ray energy and a second training X-ray energy, the second training X-ray energy differing from the first training X-ray energy;
determining a comparison difference image data record of the training examination volume;
determining a training difference image data record of the training examination volume by application of the trained function to input data, the input data being based upon the first training real image data record and being based upon the multi-energetic training real image data record;
adapting the trained function based upon a comparison of the training difference image data record and the comparison difference image data record; and
providing the trained function.

16. The method of claim 15, further comprising:
determining a mask image data record of the training examination volume, wherein the comparison difference image data record is determined by way of a digital subtraction angiography based upon the mask image data record and the first training real image data record or the comparison difference image data record is determined by way of a digital subtraction angiography based upon the mask image data record and the multi-energetic training real image data record.

17. The method of claim 16, further comprising:
receiving a first three-dimensional material model of the training examination volume, wherein at least one of the first training real image data record and the multi-energetic training real image data record is based upon a simulation of an interaction between X-ray radiation and the first three-dimensional material model.

18. The method of claim 17, further comprising:
receiving a second three-dimensional material model of the training examination volume,
wherein the first three-dimensional material model is a material model of the training examination volume including contrast medium,
wherein the second three-dimensional material model is a material model of the training examination volume without contrast medium,
wherein the mask image data record is based upon a simulation of an interaction between X-ray radiation and the second three-dimensional material model.

19. A provision system for providing a difference image data record of an examination volume, comprising:
an interface; and
a computer unit, at least one of the interface and the computer unit being configured to
determine a first real image data record of the examination volume in respect of a first X-ray energy,
determine a multi-energetic real image data record of the examination volume in respect of the first X-ray energy and a second X-ray energy, the second X-ray energy differing from the first X-ray energy, and
determine the difference image data record of the examination volume by application of a trained function to input data, the input data being based upon the first real image data record and the multi-energetic real image data record, and
wherein the interface is further configured to provide the difference image data record.

20. An X-ray device, comprising the provision system of claim 19.

21. A training system for providing a trained function, comprising:
a training interface; and
a training computer unit, at least one of the training interface and the training computer unit being configured to
determine a first training real image data record of a training examination volume in respect of a first training X-ray energy,
determine a multi-energetic training real image data record of the training examination volume in respect of the first training X-ray energy and a second training X-ray energy, the second training X-ray energy differing from the first training X-ray energy, determine a comparison difference image data record of the training examination volume, and determine a training difference image data record of the training examination volume by application of the trained function to input data, the input data being based upon the first training real image data record and upon the multi-energetic training real image data record, wherein the training computer unit is further configured to adapt the trained function based upon a comparison of the training difference image data record and the comparison difference image data record, and wherein the training interface is further configured to provide the trained function.

22. A non-transitory computer program product storing a computer program, directly loadable into a memory store of a provision system, including program portions to carry out the method of claim 1 when the program portions are executed by the provision system.

23. A non-transitory computer-readable storage medium storing program portions, readable and executable by a provision system to carry out the method of claim 1 when the program portions are executed by the provision system.

24. A non-transitory computer-readable storage medium storing program portions, readable and executable by a training system to carry out the method of claim 15 when the program portions are executed by the training system.

25. The method of claim 2, further comprising:
receiving first X-ray projections of the examination volume in respect of the first X-ray energy;
receiving second X-ray projections of the examination volume in respect of the second X-ray energy, wherein at least one of
the first real image data record is at least one of based upon the first X-ray projections and includes the first X-ray projections,
the second real image data record is at least one of based upon the second X-ray projections and includes the second X-ray projections, and
the multi-energetic real image data record is at least one of based upon the first X-ray projections and the second X-ray projections and includes the first X-ray projections and the second X-ray projections.

26. The method of claim 25, wherein at least one of
the first real image data record is based upon an at least three-dimensional reconstruction of the first X-ray projections;
the second real image data record is an at least three-dimensional reconstruction of the second X-ray projections; and
the multi-energetic real image data record is an at least three-dimensional reconstruction of the first X-ray projections and the second X-ray projections.

27. The method of claim 4, wherein at least one of
during recording of the first X-ray projections, the examination volume includes contrast medium, and
during recording of the second X-ray projections, the examination volume includes contrast medium.

28. The method of claim 4, wherein the first X-ray projections and the second X-ray projections have been recorded simultaneously.

29. The method of claim 10, wherein at least one of
an overlap of the first projection angle region and the second projection angle region comprises at least 75% of at least one of the first projection angle region and of the second projection angle region.

30. The method of claim 10, wherein at least one of
an overlap of the first projection angle region and the second projection angle region comprises at least 90% of at least one of the first projection angle region and of the second projection angle region.

31. The method of claim 1, wherein output data of the trained function includes a probability data record, wherein the difference image data record is based upon the probability data record.

32. The method of claim 13, wherein the difference image data record is based upon a multiplication of the probability data record by the first real image data record.

33. The method of claim 16, further comprising:
receiving a first three-dimensional material model of the training examination volume, wherein at least one of the first training real image data record and the multi-energetic training real image data record is based upon a simulation of an interaction between X-ray radiation and the first three-dimensional material model.

34. The method of claim 33, further comprising:
receiving a second three-dimensional material model of the training examination volume,
wherein the first three-dimensional material model is a material model of the training examination volume including contrast medium,
wherein the second three-dimensional material model is a material model of the training examination volume without contrast medium,
wherein the mask image data record is based upon a simulation of an interaction between X-ray radiation and the second three-dimensional material model.

35. A non-transitory computer program product storing a computer program, directly loadable into a training memory store of a training system, including program portions to carry out the method of claim 15 when the program portions are executed by the training system.

36. A computer program or computer-readable storage medium comprising a trained function provided by the method of claim 15.

* * * * *